US012797186B2

(12) # United States Patent
Watanabe et al.

(10) Patent No.: US 12,797,186 B2
(45) Date of Patent: Nov. 17, 2026

(54) INTRAOCULAR LENS INJECTOR

(71) Applicant: Hoya Medical Singapore Pte. Ltd., Singapore (SG)

(72) Inventors: Yoshitaka Watanabe, Tokyo (JP); Tadashi Ito, Saitama (JP)

(73) Assignee: Hoya Medical Singapore Pte. Ltd., Singapore (SG)

( * ) Notice: Subject to any disclaimer, the term of this patent is extended or adjusted under 35 U.S.C. 154(b) by 731 days.

(21) Appl. No.: 17/801,364

(22) PCT Filed: Dec. 24, 2020

(86) PCT No.: PCT/JP2020/048495
§ 371 (c)(1),
(2) Date: Aug. 22, 2022

(87) PCT Pub. No.: WO2021/171770
PCT Pub. Date: Sep. 2, 2021

(65) Prior Publication Data
US 2023/0033115 A1 Feb. 2, 2023

(30) Foreign Application Priority Data
Feb. 28, 2020 (JP) ................................ 2020-033060
Feb. 28, 2020 (JP) ................................ 2020-033061

(51) Int. Cl.
*A61F 2/16* (2006.01)

(52) U.S. Cl.
CPC ............ *A61F 2/167* (2013.01); *A61F 2/1648* (2013.01); *A61F 2/1613* (2013.01)

(58) Field of Classification Search
CPC ....... A61F 2/1662; A61F 2/167; A61F 2/1672
See application file for complete search history.

(56) References Cited

U.S. PATENT DOCUMENTS

| | | | |
|---|---|---|---|
| 2,761,446 | A | 9/1956 | Reed |
| 3,212,685 | A | 10/1965 | Swan |
| 4,205,747 | A | 6/1980 | Gilliam et al. |

(Continued)

FOREIGN PATENT DOCUMENTS

| | | | |
|---|---|---|---|
| CN | 101073519 | A | 11/2007 |
| CN | 204601363 | U | 9/2015 |

(Continued)

OTHER PUBLICATIONS

U.S. Appl. No. 12/602,442, filed Dec. 15, 2009, U.S. Pat. No. 8,747,465.

(Continued)

*Primary Examiner* — Todd J Scherbel
(74) *Attorney, Agent, or Firm* — Henricks Slavin LLP

(57) ABSTRACT

Provided is an intraocular lens injector 1 for injecting an intraocular lens 4 into an eye. The intraocular lens injector 1 includes a hollow body, a lens setting portion 11 provided inside the hollow body, and a slider 6 for advancing the intraocular lens 4 set on the lens setting portion 11. A space 72 into which a part of the rear side of the intraocular lens 4 is capable of moving downward is provided at a position α on the inner-circumference lower portion of the hollow body, a front limit of a range of motion of a portion of the slider 6 that abuts against the outer circumference of an optical portion 41 of the intraocular lens 4 being encompassed above the position α.

19 Claims, 11 Drawing Sheets

(56) References Cited

U.S. PATENT DOCUMENTS 4,269,307 A 5/1981 LaHaye
4,423,809 A 1/1984 Mazzocco
4,573,998 A 3/1986 Mazzocco
4,608,049 A 8/1986 Kelman
4,634,423 A 1/1987 Bailey
4,681,102 A 7/1987 Bartell
4,697,697 A 10/1987 Graham et al.
4,699,140 A 10/1987 Holmes
4,702,244 A 10/1987 Mazzocco
4,715,373 A 12/1987 Mazzocco et al.
4,747,404 A 5/1988 Jampel et al.
4,750,498 A 6/1988 Graham
4,759,359 A 7/1988 Willis et al.
4,763,650 A 8/1988 Hauser
4,765,329 A 8/1988 Cumming et al.
4,769,034 A 9/1988 Poley
4,781,719 A 11/1988 Kelman
4,787,904 A 11/1988 Severin
4,810,249 A 3/1989 Haber et al.
4,819,631 A 4/1989 Poley
4,834,094 A 5/1989 Patton
4,836,201 A 6/1989 Patton
4,862,885 A 9/1989 Cumming
4,880,000 A 11/1989 Holmes et al.
4,919,130 A 4/1990 Stoy et al.
4,934,363 A 6/1990 Smith et al.
4,955,889 A 9/1990 Van Gent
4,976,716 A 12/1990 Cumming
4,988,352 A 1/1991 Poley
4,994,028 A 2/1991 Leonard et al.
5,066,297 A 11/1991 Cumming
5,098,439 A 3/1992 Hill et al.
5,123,905 A 6/1992 Kelman
5,139,501 A 8/1992 Klaas
5,171,241 A 12/1992 Buboltz et al.
5,176,686 A 1/1993 Poley
5,178,622 A 1/1993 Lehner, II
5,190,552 A 3/1993 Kelman
5,190,553 A 3/1993 Kanert et al.
5,222,972 A 6/1993 Hill et al.
5,242,450 A 9/1993 McDonald
5,259,395 A 11/1993 Li
5,275,604 A 1/1994 Rheinish et al.
5,281,227 A 1/1994 Sussman
5,304,182 A 4/1994 Rheinish et al.
5,354,333 A 10/1994 Kammann et al.
5,395,378 A 3/1995 McDonald
5,425,734 A 6/1995 Blake
5,454,818 A 10/1995 Hambleton et al.
5,468,246 A 11/1995 Blake
5,474,562 A 12/1995 Orchowski et al.
5,494,484 A 2/1996 Feingold
5,496,328 A 3/1996 Nakajima et al.
5,499,987 A 3/1996 Feingold
5,562,676 A 10/1996 Brady et al.
5,571,113 A 11/1996 McDonald
5,578,042 A 11/1996 Cumming
5,582,613 A 12/1996 Brady
5,582,614 A 12/1996 Feingold
5,584,304 A 12/1996 Brady
5,616,148 A 4/1997 Eagles et al.
5,620,450 A 4/1997 Eagles et al.
5,643,275 A 7/1997 Blake
5,643,276 A 7/1997 Zaleski
5,645,534 A 7/1997 Chanoch
5,653,715 A 8/1997 Reich et al.
5,653,753 A 8/1997 Brady et al.
5,702,402 A 12/1997 Brady
5,702,441 A 12/1997 Zhou
5,716,364 A 2/1998 Makker et al.
5,728,075 A 3/1998 Levander
5,728,102 A 3/1998 Feingold et al.
5,735,858 A 4/1998 Makker et al.
5,766,181 A 6/1998 Chambers et al.
5,772,666 A 6/1998 Feingold et al.
5,772,667 A 6/1998 Blake
5,776,138 A 7/1998 Vidal et al.
5,800,442 A 9/1998 Wolf et al.
5,803,925 A 9/1998 Yang et al.
5,807,400 A 9/1998 Chambers et al.
5,810,833 A 9/1998 Brady et al.
5,810,834 A 9/1998 Heyman
5,860,984 A 1/1999 Chambers et al.
5,860,986 A 1/1999 Reich et al.
5,868,751 A 2/1999 Feingold
5,868,752 A 2/1999 Makker et al.
5,873,879 A 2/1999 Figueroa et al.
5,876,406 A 3/1999 Wolf et al.
5,876,407 A 3/1999 Makker et al.
5,876,440 A 3/1999 Feingold
5,891,152 A 4/1999 Feingold
5,902,307 A 5/1999 Feingold et al.
5,919,197 A 7/1999 McDonald
5,921,989 A 7/1999 Deacon et al.
5,928,245 A 7/1999 Wolf et al.
5,941,886 A 8/1999 Feingold
5,942,277 A 8/1999 Makker et al.
5,944,725 A 8/1999 Cicenas
5,947,974 A 9/1999 Brady et al.
5,947,975 A 9/1999 Kikuchi et al.
5,957,748 A 9/1999 Ichiha
5,957,896 A 9/1999 Bendek et al.
6,001,107 A 12/1999 Feingold
6,010,510 A 1/2000 Brown et al.
6,022,358 A 2/2000 Wolf et al.
6,048,348 A 4/2000 Chambers et al.
6,050,999 A 4/2000 Paraschac et al.
6,051,000 A 4/2000 Heyman
6,056,757 A 5/2000 Feingold et al.
6,056,758 A 5/2000 Vidal et al.
6,059,791 A 5/2000 Chambers
6,074,397 A 6/2000 Chambers et al.
6,083,230 A 7/2000 Makker et al.
6,093,193 A 7/2000 Makker et al.
6,129,733 A 10/2000 Brady et al.
6,142,999 A 11/2000 Brady et al.
6,143,000 A 11/2000 Feingold
6,162,229 A 12/2000 Feingold et al.
6,174,315 B1 1/2001 Chambers et al.
6,214,015 B1 4/2001 Reich et al.
6,241,737 B1 6/2001 Feingold
6,248,111 B1 6/2001 Glick et al.
6,251,114 B1 6/2001 Farmer et al.
6,254,607 B1 7/2001 Makker et al.
6,267,768 B1 7/2001 Deacon
6,283,975 B1 9/2001 Glick et al.
6,283,976 B1 9/2001 Portney
6,312,433 B1 11/2001 Butts
6,334,862 B1 1/2002 Vidal et al.
6,336,932 B1 1/2002 Figueroa et al.
6,355,046 B2 3/2002 Kikuchi et al.
6,371,960 B2 4/2002 Heyman et al.
6,386,357 B1 5/2002 Egawa
6,387,101 B1 5/2002 Butts et al.
6,398,788 B1 6/2002 Makker et al.
6,406,481 B2 6/2002 Feingold et al.
6,428,545 B2 8/2002 Portney
6,447,519 B1 9/2002 Brady et al.
6,447,520 B1 9/2002 Ott et al.
6,468,282 B2 10/2002 Kikuchi et al.
6,471,708 B2 10/2002 Green
6,491,697 B1 12/2002 Clark et al.
6,497,708 B1 12/2002 Cumming
6,500,181 B1 12/2002 Portney
6,503,275 B1 1/2003 Cumming
6,506,195 B2 1/2003 Chambers et al.
6,537,283 B2 3/2003 Van Noy
6,540,754 B2 4/2003 Brady
6,554,839 B2 4/2003 Brady
6,558,395 B2 5/2003 Hjertman et al.
6,605,093 B1 8/2003 Blake
6,607,537 B1 8/2003 Binder
6,629,979 B1 10/2003 Feingold
6,666,871 B2 12/2003 Kikuchi et al.

(56) References Cited

U.S. PATENT DOCUMENTS

| | | | |
|---|---|---|---|
| 6,679,891 | B2 | 1/2004 | Makker et al. |
| 6,685,740 | B2 | 2/2004 | Figueroa et al. |
| 6,712,848 | B1 | 3/2004 | Wolf et al. |
| 6,723,104 | B2 | 4/2004 | Ott |
| 6,733,507 | B2 | 5/2004 | McNicholas et al. |
| 6,749,631 | B1 | 6/2004 | Pietrini et al. |
| 6,793,674 | B2 | 9/2004 | Zapata |
| 6,858,033 | B2 | 2/2005 | Kobayashi |
| 6,921,405 | B2 | 7/2005 | Feingold et al. |
| 6,923,815 | B2 | 8/2005 | Brady et al. |
| 6,976,989 | B1 | 12/2005 | Vincent |
| 7,014,641 | B2 | 3/2006 | Kobayashi et al. |
| 7,025,782 | B2 | 4/2006 | Kobayashi et al. |
| 7,033,366 | B2 | 4/2006 | Brady |
| 7,037,312 | B2 | 5/2006 | Kikuchi et al. |
| 7,074,227 | B2 | 7/2006 | Portney |
| 7,097,649 | B2 | 8/2006 | Meyer |
| 7,131,976 | B2 | 11/2006 | Kobayashi et al. |
| 7,156,854 | B2 | 1/2007 | Brown et al. |
| 7,348,038 | B2 | 3/2008 | Makker et al. |
| 7,422,604 | B2 | 9/2008 | Vaquero et al. |
| 7,429,263 | B2 | 9/2008 | Vaquero et al. |
| 7,458,976 | B2 | 12/2008 | Peterson et al. |
| 7,476,230 | B2 | 1/2009 | Ohno et al. |
| 7,494,505 | B2 | 2/2009 | Kappelhof et al. |
| 7,645,300 | B2 | 1/2010 | Tsai |
| 8,273,122 | B2 | 9/2012 | Anderson |
| 8,382,769 | B2 | 2/2013 | Inoue |
| 8,460,311 | B2 | 6/2013 | Ishii |
| 8,470,032 | B2 | 6/2013 | Inoue et al. |
| 8,475,526 | B2 | 7/2013 | Pynson |
| 8,475,528 | B2 | 7/2013 | Ichinohe et al. |
| 8,523,877 | B2 | 9/2013 | Ichinohe et al. |
| 8,523,941 | B2 | 9/2013 | Ichinohe et al. |
| 8,535,375 | B2 | 9/2013 | Ichinohe et al. |
| 8,545,512 | B2 | 10/2013 | Ichinohe et al. |
| 8,574,239 | B2 | 11/2013 | Ichinohe et al. |
| 8,603,103 | B2 | 12/2013 | Kudo et al. |
| 8,647,382 | B2 | 2/2014 | Kudo et al. |
| 8,702,795 | B2 | 4/2014 | Shoji et al. |
| 8,747,465 | B2 | 6/2014 | Someya et al. |
| 8,968,328 | B2 | 3/2015 | Ichinohe et al. |
| 9,114,006 | B2 | 8/2015 | Inoue |
| 9,114,007 | B2 | 8/2015 | Ichinohe et al. |
| 9,186,246 | B2 | 11/2015 | Inoue |
| 9,220,593 | B2 | 12/2015 | Ichinohe |
| 9,237,947 | B2 | 1/2016 | Valle |
| 9,289,288 | B2 | 3/2016 | Someya et al. |
| 9,314,373 | B2 | 4/2016 | Kudo et al. |
| 9,326,847 | B2 | 5/2016 | Sanger |
| 9,364,320 | B2 | 6/2016 | Ichinohe et al. |
| 9,554,894 | B2 | 1/2017 | Inoue |
| 9,572,710 | B1 | 2/2017 | Kudo et al. |
| 9,655,718 | B2 | 5/2017 | Kudo |
| 9,687,340 | B2 | 6/2017 | Anderson |
| 9,877,826 | B2 | 1/2018 | Kudo et al. |
| 9,901,442 | B2 | 2/2018 | Kudo et al. |
| 9,907,647 | B2 | 3/2018 | Inoue |
| 9,980,811 | B2 | 5/2018 | Kudo et al. |
| 10,039,668 | B2 | 8/2018 | Kudo et al. |
| 10,231,826 | B2 | 3/2019 | Hangya et al. |
| 10,383,723 | B2 | 8/2019 | Kudo |
| 10,390,940 | B2 | 8/2019 | Someya et al. |
| 10,405,971 | B2 | 9/2019 | Someya et al. |
| 10,517,717 | B2 | 12/2019 | Inoue |
| 10,799,339 | B2 | 10/2020 | Kudo et al. |
| 10,849,738 | B2 | 12/2020 | Kudo et al. |
| 11,033,382 | B2 | 6/2021 | Watanabe et al. |
| 11,439,499 | B2 | 9/2022 | Wensrich et al. |
| 11,938,019 | B2 | 3/2024 | Someya et al. |
| 12,076,231 | B2 | 9/2024 | Noda et al. |
| 12,257,145 | B2 | 3/2025 | Kudo |
| 12,414,852 | B2 | 9/2025 | Watanabe |
| 12,478,467 | B2 | 11/2025 | Kudo |
| 2001/0007942 | A1 | 7/2001 | Kikuchi et al. |
| 2001/0020171 | A1 | 9/2001 | Heyman |
| 2002/0082609 | A1 | 6/2002 | Green |
| 2002/0103490 | A1 | 8/2002 | Brady |
| 2002/0151904 | A1 | 10/2002 | Feingold et al. |
| 2002/0165610 | A1 | 11/2002 | Waldock |
| 2002/0193805 | A1 | 12/2002 | Ott et al. |
| 2003/0036765 | A1 | 2/2003 | Van Noy |
| 2003/0040755 | A1 | 2/2003 | Meyer |
| 2003/0050647 | A1 | 3/2003 | Brady |
| 2003/0088253 | A1 | 5/2003 | Seil |
| 2003/0139749 | A1 | 7/2003 | Kikuchi et al. |
| 2003/0181921 | A1 | 9/2003 | Jeannin |
| 2003/0195522 | A1 | 10/2003 | McNicholas |
| 2003/0212406 | A1 | 11/2003 | Kobayashi et al. |
| 2003/0212407 | A1 | 11/2003 | Kikuchi |
| 2003/0212408 | A1 | 11/2003 | Kobayashi |
| 2003/0212409 | A1 | 11/2003 | Kobayashi et al. |
| 2004/0039345 | A1 | 2/2004 | Benz et al. |
| 2004/0111094 | A1 | 6/2004 | Meyer |
| 2004/0116937 | A1 | 6/2004 | Portney |
| 2004/0117012 | A1 | 6/2004 | Vincent |
| 2004/0127911 | A1 | 7/2004 | Figueroa |
| 2004/0147938 | A1 | 7/2004 | Dusek et al. |
| 2004/0186428 | A1 | 9/2004 | Ray |
| 2004/0238392 | A1 | 12/2004 | Peterson et al. |
| 2004/0243141 | A1 | 12/2004 | Brown et al. |
| 2005/0033308 | A1 | 2/2005 | Callahan et al. |
| 2005/0049605 | A1 | 3/2005 | Vaquero et al. |
| 2005/0049606 | A1 | 3/2005 | Vaquero et al. |
| 2005/0055011 | A1 | 3/2005 | Enggaard |
| 2005/0125000 | A1 | 6/2005 | Tourrette et al. |
| 2005/0143750 | A1 | 6/2005 | Vaquero |
| 2005/0182419 | A1 | 8/2005 | Tsai |
| 2005/0222578 | A1 | 10/2005 | Vaquero |
| 2005/0261703 | A1 | 11/2005 | Feingold et al. |
| 2006/0085013 | A1 | 4/2006 | Dusek |
| 2006/0142781 | A1 | 6/2006 | Pynson et al. |
| 2006/0167466 | A1 | 7/2006 | Dusek |
| 2006/0173540 | A1 | 8/2006 | Vincent |
| 2006/0200167 | A1 | 9/2006 | Peterson et al. |
| 2006/0229633 | A1 | 10/2006 | Shepherd |
| 2006/0235429 | A1 | 10/2006 | Lee et al. |
| 2006/0293694 | A1 | 12/2006 | Futamura |
| 2007/0000801 | A1 | 1/2007 | Mauran et al. |
| 2007/0005135 | A1 | 1/2007 | Makker et al. |
| 2007/0168026 | A1 | 7/2007 | Nagasaka |
| 2007/0173860 | A1 | 7/2007 | Iwasaki |
| 2007/0270945 | A1 | 11/2007 | Kobayashi |
| 2008/0027460 | A1 | 1/2008 | Kobayashi |
| 2008/0033449 | A1 | 2/2008 | Cole et al. |
| 2008/0058830 | A1 | 3/2008 | Cole et al. |
| 2008/0086146 | A1 | 4/2008 | Ishii et al. |
| 2008/0097459 | A1 | 4/2008 | Kammerlander et al. |
| 2008/0221584 | A1 | 9/2008 | Downer |
| 2009/0036898 | A1 | 2/2009 | Ichinohe |
| 2009/0043313 | A1 | 2/2009 | Ichinohe |
| 2009/0112223 | A1 | 4/2009 | Downer et al. |
| 2009/0125034 | A1 | 5/2009 | Pynson |
| 2009/0138022 | A1 | 5/2009 | Tu et al. |
| 2009/0204122 | A1 | 8/2009 | Ichinohe et al. |
| 2009/0216244 | A1 | 8/2009 | Pynson |
| 2009/0248031 | A1 | 10/2009 | Ichinohe |
| 2009/0270876 | A1 | 10/2009 | Hoffmann et al. |
| 2009/0292293 | A1 | 11/2009 | Bogaert et al. |
| 2010/0082037 | A1 | 4/2010 | Kobayashi et al. |
| 2010/0094309 | A1 | 4/2010 | Boukhny et al. |
| 2010/0106160 | A1 | 4/2010 | Tsai |
| 2010/0161049 | A1 | 6/2010 | Inoue |
| 2010/0185206 | A1 | 7/2010 | Ichinohe et al. |
| 2010/0217273 | A1 | 8/2010 | Someya et al. |
| 2010/0286704 | A1 | 11/2010 | Ichinohe et al. |
| 2010/0331808 | A1 | 12/2010 | Py et al. |
| 2011/0046633 | A1 | 2/2011 | Pankin et al. |
| 2011/0046635 | A1 | 2/2011 | Pankin et al. |
| 2011/0082463 | A1 | 4/2011 | Inoue |
| 2011/0098717 | A1 | 4/2011 | Inoue |
| 2011/0144654 | A1 | 6/2011 | Isaacs et al. |
| 2011/0172676 | A1 | 7/2011 | Chen |
| 2011/0264101 | A1 | 10/2011 | Inoue et al. |

(56) References Cited

U.S. PATENT DOCUMENTS

| | | | |
|---|---|---|---|
| 2011/0270264 | A1 | 11/2011 | Shoji et al. |
| 2011/0288557 | A1 | 11/2011 | Kudo et al. |
| 2012/0022548 | A1 | 1/2012 | Zacharias |
| 2012/0022549 | A1 | 1/2012 | Someya et al. |
| 2012/0071887 | A1 | 3/2012 | Ichinohe et al. |
| 2012/0123438 | A1 | 5/2012 | Horvath et al. |
| 2012/0221102 | A1 | 8/2012 | Tanaka et al. |
| 2013/0006259 | A1 | 1/2013 | Sanger |
| 2013/0018460 | A1 | 1/2013 | Anderson |
| 2013/0085507 | A1 | 4/2013 | Nagasaka |
| 2013/0226193 | A1 | 8/2013 | Kudo et al. |
| 2013/0245635 | A1 | 9/2013 | Inoue |
| 2013/0345713 | A1 | 12/2013 | Cole et al. |
| 2014/0081284 | A1 | 3/2014 | Ichinohe et al. |
| 2014/0107660 | A1 | 4/2014 | Ichinohe et al. |
| 2014/0114323 | A1 | 4/2014 | Kudo et al. |
| 2014/0135784 | A1 | 5/2014 | Maroscheck et al. |
| 2014/0180299 | A1 | 6/2014 | Ichinohe et al. |
| 2014/0180300 | A1 | 6/2014 | Ichinohe et al. |
| 2014/0194890 | A1 | 7/2014 | Kudo et al. |
| 2014/0200588 | A1 | 7/2014 | Anderson et al. |
| 2014/0276901 | A1 | 9/2014 | Auld |
| 2014/0296863 | A1 | 10/2014 | Anderson et al. |
| 2015/0045805 | A1 | 2/2015 | Kontur et al. |
| 2015/0157500 | A1 | 6/2015 | Midorikawa |
| 2015/0327992 | A1 | 11/2015 | Wagner et al. |
| 2016/0000556 | A1 | 1/2016 | Perera |
| 2016/0058554 | A1 | 3/2016 | Anderson et al. |
| 2016/0113759 | A1 | 4/2016 | Inoue |
| 2016/0151150 | A1 | 6/2016 | Sato |
| 2016/0193038 | A1 | 7/2016 | Kudo et al. |
| 2016/0256316 | A1 | 9/2016 | Van Noy |
| 2016/0270907 | A1 | 9/2016 | Attinger |
| 2016/0331587 | A1 | 11/2016 | Yamada et al. |
| 2016/0346077 | A1 | 12/2016 | Someya et al. |
| 2017/0079772 | A1 | 3/2017 | Kudo |
| 2017/0119522 | A1 | 5/2017 | Auld et al. |
| 2017/0151056 | A1 | 6/2017 | Inoue |
| 2017/0202662 | A1 | 7/2017 | Someya et al. |
| 2017/0252149 | A1 | 9/2017 | Kudo et al. |
| 2017/0252150 | A1 | 9/2017 | Kudo et al. |
| 2017/0258582 | A1 | 9/2017 | Kudo et al. |
| 2017/0354493 | A1 | 12/2017 | Andersen et al. |
| 2018/0014996 | A1 | 1/2018 | Asbaghi |
| 2018/0200046 | A1 | 7/2018 | Brown et al. |
| 2018/0200047 | A1 | 7/2018 | Wu et al. |
| 2018/0228650 | A1 | 8/2018 | Putallaz et al. |
| 2018/0250125 | A1 | 9/2018 | Kudo et al. |
| 2018/0353287 | A1 | 12/2018 | Kudo et al. |
| 2019/0151078 | A1 | 5/2019 | Watanabe et al. |
| 2019/0192284 | A1 | 6/2019 | Watanabe et al. |
| 2020/0015959 | A1 | 1/2020 | Wensrich et al. |
| 2020/0113674 | A1 | 4/2020 | Someya et al. |
| 2021/0145570 | A1 | 5/2021 | Kudo |
| 2021/0161653 | A1 | 6/2021 | Noda et al. |
| 2021/0205071 | A1 | 7/2021 | Chini |
| 2022/0151767 | A1 | 5/2022 | Kudo |
| 2023/0225858 | A1 | 7/2023 | Someya et al. |
| 2023/0301833 | A1 | 9/2023 | Wu |
| 2023/0338138 | A1 | 10/2023 | Kelp et al. |
| 2023/0372083 | A1 | 11/2023 | Kudo |
| 2024/0268951 | A1 | 8/2024 | Maroscheck et al. |
| 2024/0374376 | A1 | 11/2024 | Noda et al. |
| 2024/0415634 | A1 | 12/2024 | Kudo |

FOREIGN PATENT DOCUMENTS

| | | | |
|---|---|---|---|
| DE | 3610925 | | 10/1987 |
| DE | 4110278 | | 10/1992 |
| DE | 19544119 | A1 | 5/1997 |
| DE | 20219445 | U1 | 3/2003 |
| EP | 0363213 | | 4/1990 |
| EP | 0727966 | | 9/2003 |
| EP | 1360947 | A1 | 11/2003 |
| EP | 1502559 | A1 | 2/2005 |
| EP | 1790317 | A2 | 5/2007 |
| EP | 1808150 | A1 | 7/2007 |
| EP | 1832247 | A1 | 9/2007 |
| EP | 1338254 | B1 | 12/2008 |
| EP | 2074961 | A1 | 7/2009 |
| EP | 2255751 | A1 | 12/2010 |
| EP | 2286763 | A1 | 2/2011 |
| EP | 2286764 | A1 | 2/2011 |
| EP | 2368526 | A1 | 9/2011 |
| EP | 2574308 | A2 | 4/2013 |
| EP | 2853236 | A2 | 4/2015 |
| EP | 3391855 | A1 | 10/2018 |
| FR | 2749752 | A | 12/1997 |
| JP | 63-197453 | A | 8/1988 |
| JP | 4-212350 | A | 8/1992 |
| JP | 5-103803 | A | 4/1993 |
| JP | 5-103808 | | 4/1993 |
| JP | 5-103809 | | 4/1993 |
| JP | 08-019558 | A | 1/1996 |
| JP | 8-024282 | A | 1/1996 |
| JP | 8-505540 | | 6/1996 |
| JP | 9-506285 | A | 6/1997 |
| JP | 11-113939 | A | 4/1999 |
| JP | 11-506357 | A | 6/1999 |
| JP | 2000-516487 | A | 12/2000 |
| JP | 2000-516488 | A | 12/2000 |
| JP | 2001-502563 | | 2/2001 |
| JP | 2001-104347 | A | 4/2001 |
| JP | 2001-259033 | | 9/2001 |
| JP | 2002-516709 | A | 6/2002 |
| JP | 2002-355268 | A | 12/2002 |
| JP | 2002-541912 | A | 12/2002 |
| JP | 2003-144480 | A | 5/2003 |
| JP | 3412106 | B2 | 6/2003 |
| JP | 2003-210498 | A | 7/2003 |
| JP | 2003-527162 | A | 9/2003 |
| JP | 2003-325569 | A | 11/2003 |
| JP | 2003-325570 | A | 11/2003 |
| JP | 2003-325572 | A | 11/2003 |
| JP | 2004-024854 | A | 1/2004 |
| JP | 2004-041271 | A | 2/2004 |
| JP | 2004-188194 | A | 7/2004 |
| JP | 2004-344213 | A | 12/2004 |
| JP | 2004-351196 | A | 12/2004 |
| JP | 2006-014963 | A | 1/2006 |
| JP | 2006-181269 | A | 7/2006 |
| JP | 2006-297146 | A | 11/2006 |
| JP | 2006-333924 | A | 12/2006 |
| JP | 2006-333980 | A | 12/2006 |
| JP | 2006-333981 | A | 12/2006 |
| JP | 2007-503872 | A | 3/2007 |
| JP | 2007-152010 | A | 6/2007 |
| JP | 2007-181604 | A | 7/2007 |
| JP | 2007-222309 | A | 9/2007 |
| JP | 2007-244570 | A | 9/2007 |
| JP | 2007-526091 | A | 9/2007 |
| JP | 2007-307168 | A1 | 11/2007 |
| JP | 2008-012016 | A | 1/2008 |
| JP | 2008-521535 | A | 6/2008 |
| JP | 2008-212689 | A | 9/2008 |
| JP | 2008-237274 | A | 10/2008 |
| JP | 2009-028223 | A | 2/2009 |
| JP | 2009-072221 | A | 4/2009 |
| JP | 2011-019987 | A | 2/2011 |
| JP | 2011-087976 | A | 5/2011 |
| JP | 2011-160858 | A | 8/2011 |
| JP | 2011-160859 | A | 8/2011 |
| JP | 2013-144163 | A | 7/2013 |
| JP | 2014-050484 | A | 3/2014 |
| JP | 2014-079630 | A | 5/2014 |
| JP | 2016049321 | A | 4/2016 |
| JP | 2016-137122 | A | 8/2016 |
| JP | 2022-039196 | A | 3/2022 |
| JP | 2025-079474 | A | 5/2025 |
| WO | WO9407436 | A1 | 4/1994 |
| WO | WO9513022 | A1 | 5/1995 |
| WO | WO9628122 | A1 | 9/1996 |
| WO | WO9715253 | A1 | 5/1997 |
| WO | WO9812969 | A1 | 4/1998 |

(56) References Cited

FOREIGN PATENT DOCUMENTS

| | | | |
|---|---|---|---|
| WO | WO9937247 | A1 | 7/1999 |
| WO | WO9958086 | A1 | 11/1999 |
| WO | WO9959668 | A1 | 11/1999 |
| WO | WO0045746 | A1 | 8/2000 |
| WO | WO0062712 | A1 | 10/2000 |
| WO | WO2002071982 | A1 | 9/2002 |
| WO | WO2002096322 | A1 | 12/2002 |
| WO | WO2004041323 | A2 | 5/2004 |
| WO | WO2004105649 | A1 | 12/2004 |
| WO | WO2005023154 | A1 | 3/2005 |
| WO | WO2005030097 | A1 | 4/2005 |
| WO | WO2005070341 | A1 | 8/2005 |
| WO | WO2005084588 | A1 | 9/2005 |
| WO | WO2006070628 | A1 | 7/2006 |
| WO | WO2006080191 | A1 | 8/2006 |
| WO | WO2006090531 | A1 | 8/2006 |
| WO | WO2007037223 | A1 | 4/2007 |
| WO | WO2007080869 | A1 | 7/2007 |
| WO | WO2007097221 | A1 | 8/2007 |
| WO | WO2008149794 | A1 | 12/2008 |
| WO | WO2008149795 | A1 | 12/2008 |
| WO | WO2009058929 | A1 | 7/2009 |
| WO | WO2009148091 | A1 | 12/2009 |
| WO | WO2010028873 | A1 | 3/2010 |
| WO | WO2010064970 | A1 | 6/2010 |
| WO | WO2011126144 | A1 | 10/2011 |
| WO | WO2011155636 | A1 | 12/2011 |
| WO | WO2012086797 | A1 | 6/2012 |
| WO | WO2012155887 | A1 | 11/2012 |
| WO | WO2015012312 | A1 | 1/2015 |
| WO | WO2016191764 | A1 | 12/2016 |
| WO | WO2018151141 | A1 | 8/2018 |
| WO | WO2019130028 | A1 | 7/2019 |

OTHER PUBLICATIONS

U.S. Appl. No. 13/244,449, filed Sep. 24, 2011, U.S. Pat. No. 9,289,288.
U.S. Appl. No. 15/063,395, filed Mar. 7, 2016, U.S. Pat. No. 10,390,940.
U.S. Appl. No. 15/476,717, filed Mar. 31, 2017, U.S. Pat. No. 10,405,971.
U.S. Appl. No. 16/550,144, filed Aug. 23, 2019, US 20200113674A1.
U.S. Appl. No. 12/602,454, filed Dec. 15, 2009, U.S. Pat. No. 8,475,528.
U.S. Appl. No. 13/244,452, filed Sep. 24, 2011, U.S. Pat. No. 8,535,375.
U.S. Appl. No. 12/667,510, filed Dec. 31, 2009, U.S. Pat. No. 9,114,006.
U.S. Appl. No. 14/812,104, filed Jul. 29, 2015, U.S. Pat. No. 9,907,647.
U.S. Appl. No. 12/995,263, filed Dec. 15, 2010, U.S. Pat. No. 9,554,894.
U.S. Appl. No. 15/382,377, filed Dec. 16, 2016, U.S. Pat. No. 10,517,717.
U.S. Appl. No. 12/997,651, filed Dec. 13, 2010, U.S. Pat. No. 8,382,769.
U.S. Appl. No. 13/757,790, filed Feb. 2, 2012, U.S. Pat. No. 9,186,246.
U.S. Appl. No. 13/583,216, filed Apr. 6, 2011, U.S. Pat. No. 9,326,847.
U.S. Appl. No. 13/699,708, filed Jun. 8, 2011, U.S. Pat. No. 8,647,382.
U.S. Appl. No. 14/145,846, filed Dec. 31, 2013, U.S. Pat. No. 9,314,373.
U.S. Appl. No. 15/071,880, filed Mar. 16, 2016, U.S. Pat. No. 10,039,668.
U.S. Appl. No. 15/336,678, filed Oct. 27, 2016, U.S. Pat. No. 9,572,710.
U.S. Appl. No. 15/608,895, filed May 30, 2017, U.S. Pat. No. 9,980,811.
U.S. Appl. No. 13/059,401, filed Feb. 16, 2011, U.S. Pat. No. 8,702,795.
U.S. Appl. No. 13/061,143, filed Feb. 26, 2011, U.S. Pat. No. 8,470,032.
U.S. Appl. No. 13/143,322, filed Jul. 5, 2011, U.S. Pat. No. 8,603,103.
U.S. Appl. No. 14/099,989, filed Dec. 8, 2013, U.S. Pat. No. 9,655,718.
U.S. Appl. No. 15/600,679, filed May 19, 2017, U.S. Pat. No. 9,877,826.
U.S. Appl. No. 15/600,684, filed May 19, 2017, U.S. Pat. No. 9,901,442.
U.S. Appl. No. 11/814,508, filed Jul. 23, 2007, U.S. Pat. No. 8,545,512.
U.S. Appl. No. 14/033,888, filed Sep. 23, 2013, U.S. Pat. No. 9,220,593.
U.S. Appl. No. 11/816,676, filed Aug. 20, 2007, U.S. Pat. No. 8,523,877.
U.S. Appl. No. 13/966,209, filed Aug. 13, 2013, U.S. Pat. No. 9,364,320.
U.S. Appl. No. 12/095,172, filed May 28, 2008, U.S. Pat. No. 8,523,941.
U.S. Appl. No. 14/011,018, filed Aug. 27, 2013, U.S. Pat. No. 8,968,328.
U.S. Appl. No. 12/088,328, filed Mar. 27, 2008, U.S. Pat. No. 8,574,239.
U.S. Appl. No. 14/065,365, filed Oct. 28, 2013, U.S. Pat. No. 9,114,007.
U.S. Appl. No. 11/722,601, filed Apr. 10, 2008, U.S. Pat. No. 8,460,311.
U.S. Appl. No. 15/126,277, filed Sep. 14, 2016, U.S. Pat. No. 10,383,723.
U.S. Appl. No. 15/756,565, filed Feb. 28, 2018, U.S. Pat. No. 10,849,738.
U.S. Appl. No. 15/756,569, filed Feb. 28, 2018, U.S. Pat. No. 10,799,339.
U.S. Appl. No. 16/313,180, filed Dec. 26, 2018, US 20190192284A1.
U.S. Appl. No. 16/313,184, filed Dec. 26, 2018, U.S. Pat. No. 11,033,382.
U.S. Appl. No. 17/055,253, filed Nov. 13, 2020, US 20210161653A1.
U.S. Appl. No. 17/055,186, filed Nov. 13, 2020, US 20210145570A1.
U.S. Appl. No. 17/435,762, filed Sep. 2, 2021, US 20220151767A1.
U.S. Appl. No. 17/801,364, filed Aug. 22, 2022.
Presentation given by James P. McCulley, titled "Benefits of Newest Generation Fully Preloaded Aspheric IOL Delivery System," on Sep. 16, 2008 at the "Aspheric IOLs" free paper session of the 2008 Congress of the European Society of Cataract and Refractive Surgery, in Berlin, Germany.
U.S. Appl. No. 17/435,762, filed Sep. 2, 2021, US 20210145570A1.
PCT International Preliminary Examination Report dated Sep. 9, 2022 for PCT App. Ser. No. PCT/JP2020/048495.
U.S. Appl. No. 16/550,144, filed Aug. 23, 2019, U.S. Pat. No. 11,617,643.
U.S. Appl. No. 18/186,167, filed Mar. 18, 2023.
U.S. Appl. No. 17/801,364, filed Aug. 22, 2022, US 20230033115A1.
U.S. Appl. No. 18/044,235, filed Mar. 7, 2023.
U.S. Appl. No. 18/186,167, filed Mar. 18, 2023, US 20230225858A1.
U.S. Appl. No. 18/044,235, filed Mar. 7, 2023, US 20230372083A1.
U.S. Appl. No. 18/186,167, filed Mar. 18, 2023, U.S. Pat. No. 11,938,019.
U.S. Appl. No. 17/055,253, filed Nov. 13, 2020, U.S. Pat. No. 12,076,231.
U.S. Appl. No. 18/778,973, filed Jul. 20, 2024.
U.S. Appl. No. 17/055,186, Nov. 13, 2020, US 20210145570A1.
U.S. Appl. No. 18/694,985, filed Mar. 24, 2023.
PCT International Search Report dated Mar. 30, 2021 for PCT App. Ser. No. PCT/JP2020/048495.

INTRAOCULAR LENS INJECTOR

TECHNICAL FIELD

The present invention relates to an intraocular lens injector.

BACKGROUND ART

In cataract surgery, removal of an opacified crystalline lens by phacoemulsification and implantation of an intraocular lens into an eye after the removal of the crystalline lens are widely performed. Nowadays, a soft intraocular lens made of a soft material such as silicone elastomer is injected into an eye using an intraocular lens injector.

When injecting a soft intraocular lens into an eye, it is possible to fold the intraocular lens, and therefore, cataract surgery can be performed with a smaller corneal incision.

A method for folding an intraocular lens is known in which a slider is advanced within an intraocular lens injector to fold the intraocular lens by utilizing a decrease in the inner diameter of an injection tube toward the front side, and then the intraocular lens is advanced using a rod (in turn, a plunger) to discharge the intraocular lens from a nozzle (for example, Patent Document 1 to the applicant of the present invention).

CITATION LIST

Patent Documents

Patent Document 1: WO 2015/141085

SUMMARY OF INVENTION

Technical Problem

The inventors of the present invention found that the slider might be advanced while catching the intraocular lens. In addition, the inventors of the present invention found another problem in that, if the intraocular lens was advanced using the rod (in turn, the plunger) in such a state, the intraocular lens might be damaged. Hereinafter, reference signs used in the present specification are the same as those used in Patent Document 1.

In the present specification, in order to describe relative positional relationships between various portions of an intraocular lens injector, directions in which they move, and the like, one of the directions (X-directions) along the X-axis is referred to as a “direction X1” and the other direction as a “direction X2”, one of the directions (Y-directions) along the Y-axis is referred to as a “direction Y1” and the other direction as a “direction Y2”, and one of the directions (Z-directions) along the Z-axis is referred to as a “direction Z1” and the other direction as a “direction Z2”.

Moreover, the direction X1 is defined as a leading end side (forward, a lens advancing direction), the direction X2 is defined as a rear end side (rearward), the direction Y1 is defined as a left side (leftward), the direction Y2 is defined as a right side (rightward), the direction Z1 is defined as a top side (upward, an optical axis direction of an intraocular lens when it is set on a lens setting portion), and the direction Z2 is defined as a bottom side (downward).

Of these directions, the directions X1 and X2 correspond to a length direction of an intraocular lens injector, the directions Y1 and Y2 correspond to a width direction of the intraocular lens injector, and the directions Z1 and Z2 correspond to a height direction of the intraocular lens injector.

FIG. 1 is a schematic partial cross-sectional view of an intraocular lens injector 1 in which a slider 6 is adopted, and indicates a state in which an intraocular lens 4 is advanced on an injector main body 5 using the slider 6.

FIG. 2 is a diagram indicating a state in which, in the schematic partial cross-sectional view of the intraocular lens injector 1 shown in FIG. 1, an upward step extending upward and forward is formed somewhere between an inner-circumference lower portion 54 of the injector main body 5 and an inner-circumference lower portion 74 of an injection tube 7, and thus a rear side 4*c* of the upper surface of the intraocular lens 4 is caught between the upward step and the slider 6 while the intraocular lens 4 is being advanced.

FIG. 3 is a diagram indicating a state in which, in the schematic partial cross-sectional view of the intraocular lens injector 1 shown in FIG. 1, a downward step extending downward and forward is formed somewhere between the inner-circumference lower portion 54 of the injector main body 5 and the inner-circumference lower portion 74 of the injection tube 7, and thus the rear side 4*c* of the upper surface of the intraocular lens 4 is caught between the downward step and the slider 6 while the intraocular lens 4 is being advanced.

Somewhere between the inner-circumference lower portion 54 of the injector main body 5 and the inner-circumference lower portion 74 of the injection tube 7 may also be referred to simply as an “inner-circumference lower portion (no reference sign)”. The upward step and the downward step may also be collectively referred to as a “step”.

As shown in FIG. 1, if a configuration as designed is provided, the diameter of the hollow body may decrease from the lens setting portion 11 toward a nozzle portion 7*b*, but no step is formed at the inner-circumference lower portion. As a result, the intraocular lens 4 is pushed forward by the slider 6 without any problems, and is properly folded. Then, the folded intraocular lens 4 is advanced to the discharge hole of the nozzle portion 7*b* using a rod 10.

On the other hand, the inventors of the present invention focused on the fact that a step may be formed at the inner-circumference lower portion due to a manufacturing dimension error of the injector main body 5 or injection tube 7, a positioning error in combining the injector main body 5 and the injection tube 7, or the like. The inventors of the present invention focused on the fact that the intraocular lens 4 may be damaged as shown in FIG. 2 or FIG. 3 in that case.

The inventors of the present invention have conducted an in-depth study based on the facts on which they focused. As a result, it became clear that, in the case where a clearance larger than necessary was present between the inner circumference of the injector main body 5 or injection tube 7 and the slider, even if no step was formed, the intraocular lens 4 might be caught between the above-mentioned inner circumference and the slider (FIG. 11, which will be shown later).

It will be appreciated that the above-mentioned problems are solved by improving the manufacturing accuracy of the injector main body 5 and the injection tube 7. On the other hand, it is not practical to discard the entire intraocular lens injector 1 only for the reason that the above-mentioned step is formed. Therefore, it is necessary to search for a technique other than improving the manufacturing accuracy.

It is a technical object of the present invention to provide an intraocular lens injector capable of suppressing damage to an intraocular lens without significantly improving the manufacturing accuracy.

Solution to Problem

The inventors of the present invention have conducted an in-depth study to achieve the above-mentioned object.

The inventors of the present invention focused on the fact that, in both cases shown in FIGS. 2 and 3, the intraocular lens 4 is caught between the step and the slider 6 because there is no room for the rear side 4*c* of the intraocular lens 4. In addition, the inventors of the present invention focused on the fact that, if the intraocular lens 4 is forcedly advanced using the rod 10 while this state is maintained, the intraocular lens 4 may be damaged.

Based on this, the inventors of the present invention found that the above-mentioned problem was solved by releasing the intraocular lens 4 from being caught before the intraocular lens 4 was advanced using the rod 10. As a result, they arrived at a technique in which a space for accommodating a part of the rear side 4*c* is formed at the inner-circumference lower portion such that a front limit L of the range of motion of the slider 6 is encompassed above the inner-circumference lower portion.

FIG. 4 shows a diagram (on the right side) indicating a state in which, in the schematic partial cross-sectional view of the intraocular lens injector 1 shown in FIG. 1, even though an upward step is formed somewhere between the inner-circumference lower portion 54 of the injector main body 5 and the inner-circumference lower portion 74 of the injection tube 7, it is possible to prevent the rear side 4*c* of the upper surface of the intraocular lens 4 from being caught between the upward step and the slider 6 by forming a space 72 for accommodating a part of the rear side 4*c* of the intraocular lens 4 at the corresponding position, and a diagram (on the left side) indicating a state in which the intraocular lens is properly pushed toward the nozzle portion 7*b* using the rod 10.

FIG. 5 shows a diagram (on the right side) indicating a state in which, in the schematic partial cross-sectional view of the intraocular lens injector 1 shown in FIG. 1, even though a downward step is formed somewhere between the inner-circumference lower portion 54 of the injector main body 5 and the inner-circumference lower portion 74 of the injection tube 7, it is possible to prevent the rear side 4*c* of the upper surface of the intraocular lens 4 from being caught between the downward step and the slider 6 by forming the space 72 for accommodating a part of the rear side 4*c* of the intraocular lens 4 at the corresponding position, and a diagram (on the left side) indicating a state in which the intraocular lens is properly pushed toward the nozzle portion 7*b* using the rod 10.

In the case of employing the above-mentioned technique, even if such an error that the inner-circumference lower portion 74 of the injection tube 7 is one level higher than the inner-circumference lower portion 54 of the injector main body 5 occurs as shown in FIG. 4, or such an error that the inner-circumference lower portion 74 of the injection tube 7 is one level lower than the inner-circumference lower portion 54 of the injector main body 5 occurs as shown in FIG. 5, the rear side 4*c* of the intraocular lens 4 moves downward due to the presence of the space 72 when the rod 10 is advanced, and the intraocular lens 4 is released from being caught by the slider 6.

As a result, even when the rod 10 is advanced, it is possible to prevent the rear side 4*c* of the intraocular lens 4 from being damaged (see a portion indicated by an arrow denoted by reference sign 72). In addition, the manufacturing accuracy of the injector main body 5 and the injection tube 7 need not be significantly improved. In other words, the errors in the manufacturing accuracy become acceptable due to the accommodation space 72 provided at the inner-circumference lower portion.

Configurations obtained based on the above-mentioned findings are as follows.

A first aspect of the present invention is an intraocular lens injector for injecting an intraocular lens into an eye, including:

a hollow body;

a lens setting portion provided inside the hollow body;

a slider for advancing the intraocular lens set on the lens setting portion; and a rod for further advancing the intraocular lens that has been advanced using the slider, wherein, when a side in the optical axis direction (Z-direction) of the intraocular lens that comes into contact with the lens setting portion when the intraocular lens is set on the lens setting portion is defined as a bottom side (direction Z2), a side opposite to the bottom side is defined as a top side (direction Z1), a side toward which the intraocular lens is advanced is defined as a front side (direction X1), a side opposite to the front side is defined as a rear side (direction X2), and a direction orthogonal to the Z-direction and X-direction is defined as a width direction (Y-direction), a space into which a part of a rear side of the intraocular lens is capable of moving downward is provided at a position α on an inner-circumference lower portion of the hollow body, a front limit of a range of motion of a portion of the slider that abuts against an outer circumference of an optical portion of the intraocular lens being encompassed above the position α.

A second aspect of the present invention is the aspect according to the first aspect, wherein the hollow body includes:

an injector main body: and an injection tube that is connected to a front end portion of the injector main body, and the position α is located somewhere within a range between an inner-circumference lower portion of the injector main body and an inner-circumference lower portion of the injection tube.

A third aspect of the present invention is the aspect according to the second aspect, wherein the space is provided at an inner-circumference lower portion of a connection portion of the injection tube connected to the injector main body.

A fourth aspect of the present invention is the aspect according to any one of the first to third aspects, wherein the space is formed by cutting the position α, and as viewed from a front side, a position in a width direction of the portion of the slider that abuts against the outer circumference of the optical portion of the intraocular lens is encompassed in a position in the width direction of the space.

A fifth aspect of the present invention is the aspect according to any one of the first to fourth aspects, wherein the space has a chamfered shape.

A sixth aspect of the present invention is the aspect according to any one of the first to fifth aspects, wherein the intraocular lens is set on the lens setting portion beforehand.

Other aspects of the present invention that can be combined with the above-mentioned aspects are as follows.

The rod may also be disposed inside the hollow body constituted by the injector main body and the injection tube. The rod is coupled with a plunger, and plays a role in advancing the intraocular lens. Note that the rod and plunger may be integrally molded.

It is preferable that the slope of the chamfered surface is not too steep. The angle of the slope with respect to the XY plane is preferably 70° or less, and more preferably 50° or less. There is no limitation on the lower limit. However, if the slope angle is too small, the slope has to extend in the X-direction of the injection tube, and thus the lower limit is set to, for example, 30° or 40°.

The space may have a depth corresponding to the sum of the manufacturing errors of the components, the positioning errors of the components, and the maximum thickness of the optical portion of the intraocular lens. Specifically, the space may have a depth of 0.2 to 5.0 mm (preferably 0.5 to 2.0 mm).

The width in the Y-direction of the space may be larger by a certain margin than the width in the Y-direction of the slider lower portion. The width in the Y-direction of the space may be set to be larger by a margin of 0.1 mm or more (or 0.2 mm or more; the upper limit is, for example, 1 mm) than the width in the Y-direction of the slider lower portion. In the case of not using a specific numerical value for this margin, the width in the Y-direction of the space may be preferably, for example, 1.1 to 1.5 times as large as the width in the Y-direction of the slider lower portion.

The front limit of the range of motion of the slider lower portion is preferably located at a position in the space, for example, within a range between the rear end of the space and a position away therefrom by half (preferably ¼) the length in the front-rear direction of the space.

The intraocular lens injector may also be an intraocular lens injector for injecting an intraocular lens into an eye, including:

an injector main body constituted by a hollow body;

a lens setting portion provided inside the injector main body;

an advancing member for advancing the intraocular lens set on the lens setting portion; and an injection tube that is separate from the injector main body and is connected to a front end portion of the injector main body, wherein, when a side in the optical axis direction (Z-direction) of the intraocular lens that comes into contact with the lens setting portion when the intraocular lens is set on the lens setting portion is defined as a bottom side (direction Z2), a side opposite to the bottom side is defined as a top side (direction Z1), a side toward which the intraocular lens is advanced is defined as a front side (direction X1), a side opposite to the front side is defined as a rear side (direction X2), and a direction orthogonal to the Z-direction and X-direction is defined as a width direction (Y-direction), a space into which a part of a rear side of the intraocular lens can move downward when the intraocular lens is advanced using the advancing member is provided at the inner-circumference lower portion of a connection portion of the injection tube connected to the injector main body.

The space may be formed by cutting the inner-circumference lower portion of the connection portion of the injection tube connected to the injector main body, and as viewed from the front side, a position in the width direction of the portion of the advancing member that abuts against the outer circumference of the optical portion of the intraocular lens may be encompassed in a position in the width direction of the space.

The advancing member may be a rod for advancing the intraocular lens set on the lens setting portion.

Advantageous Effects of Invention

With the present invention, it is possible to provide an intraocular lens injector capable of suppressing damage to an intraocular lens without significantly improving the manufacturing accuracy.

DESCRIPTION OF EMBODIMENTS

Figure 1:
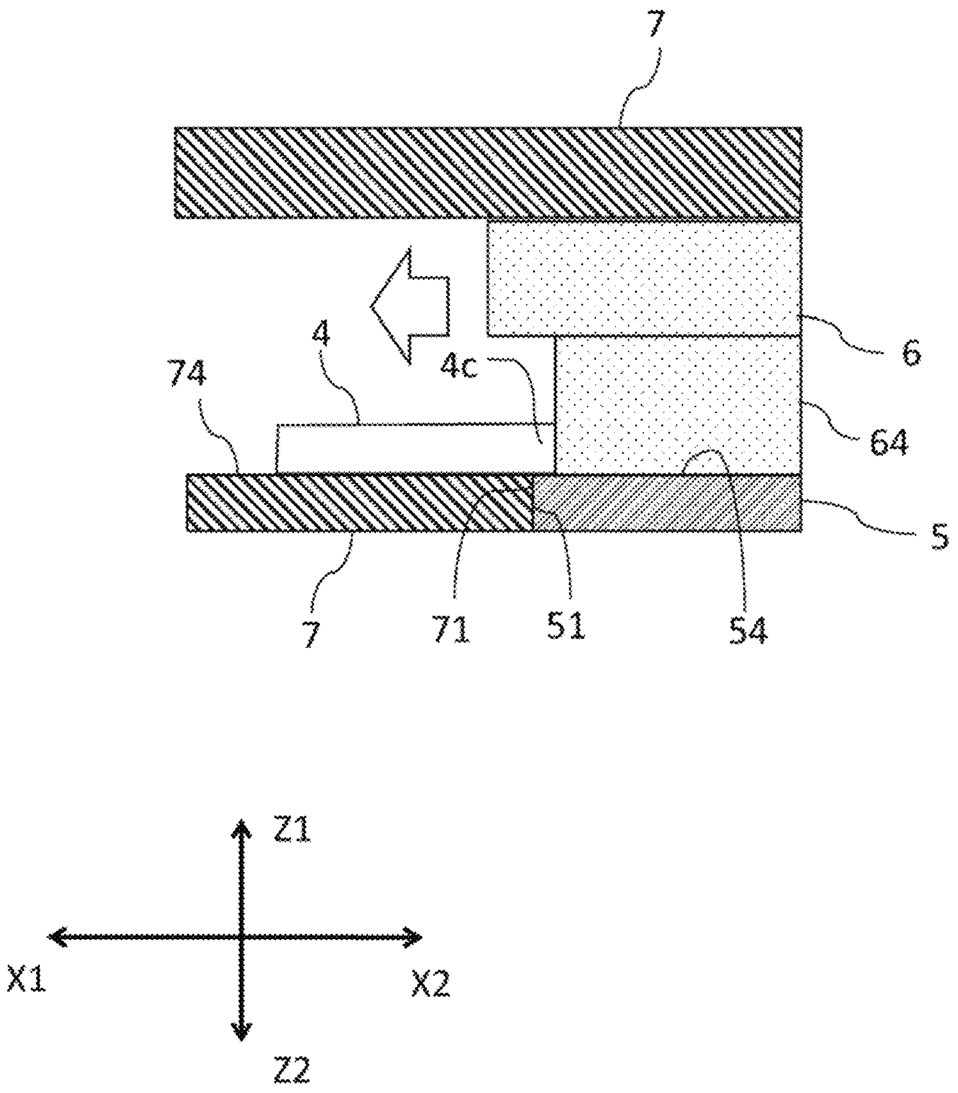
FIG. 1 is a schematic partial cross-sectional view of an intraocular lens injector that is produced by combining an injector main body and an injection tube that are separately produced and in which a slider is adopted, and indicates a state in which an intraocular lens is advanced, using the slider, on a connection portion where the injector main body and the injection tube are connected to each other.

Hereinafter, an embodiment of the present invention will be described in detail with reference to the drawings. In the present specification, "to" between numerical values means being greater than or equal to a predetermined numerical value and smaller than or equal to a predetermined numerical value.

Note that it should be mentioned in advance that main characterizing portions of the embodiment of the present invention correspond to aspects of an injector main body 5, a slider 6, and an injection tube 7 disclosed in Patent Document 1 (see, for example, FIGS. 2, 6, 8, and 10 and related descriptions thereof in Patent Document 1). For this reason, configurations of portions other than the configurations of the above-mentioned portions in an intraocular lens injector 1 are as described in Patent Document 1, and descriptions thereof are omitted or simplified. For content that is not described below, configurations disclosed in Patent Document 1 are adopted, and the description of Patent Document 1 is incorporated in the present specification in its entirety.

Embodiment 1

In Embodiment 1, a case where an intraocular lens 4 is folded using a slider 6, and then the intraocular lens 4 is released from a nozzle portion 7*b* using a plunger 9 (in turn, a rod 10) as in the case of the intraocular lens injector disclosed in Patent Document 1 is described by way of example.

Configuration of Intraocular Lens Injector

Figure 6:
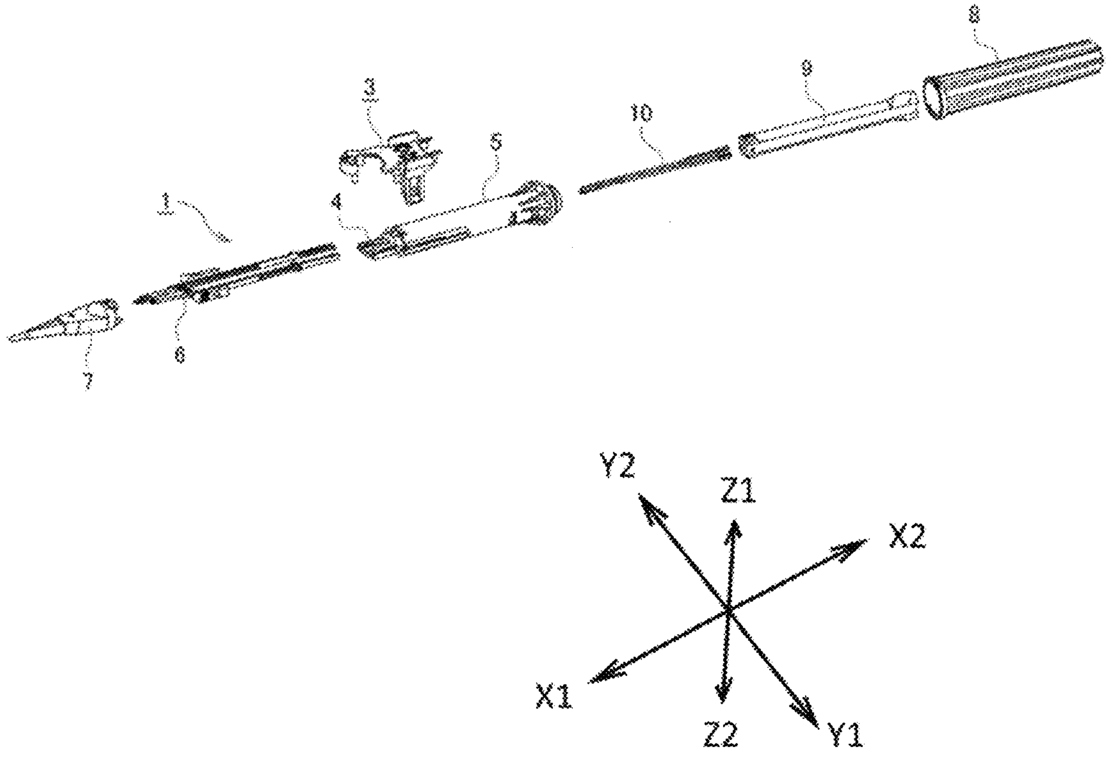
FIG. 6 is a perspective view showing a configuration example of the appearance of an intraocular lens injector according to Embodiment 1.

FIG. 6 is a perspective view showing a configuration example of the appearance of an intraocular lens injector according to Embodiment 1.

Figure 7:
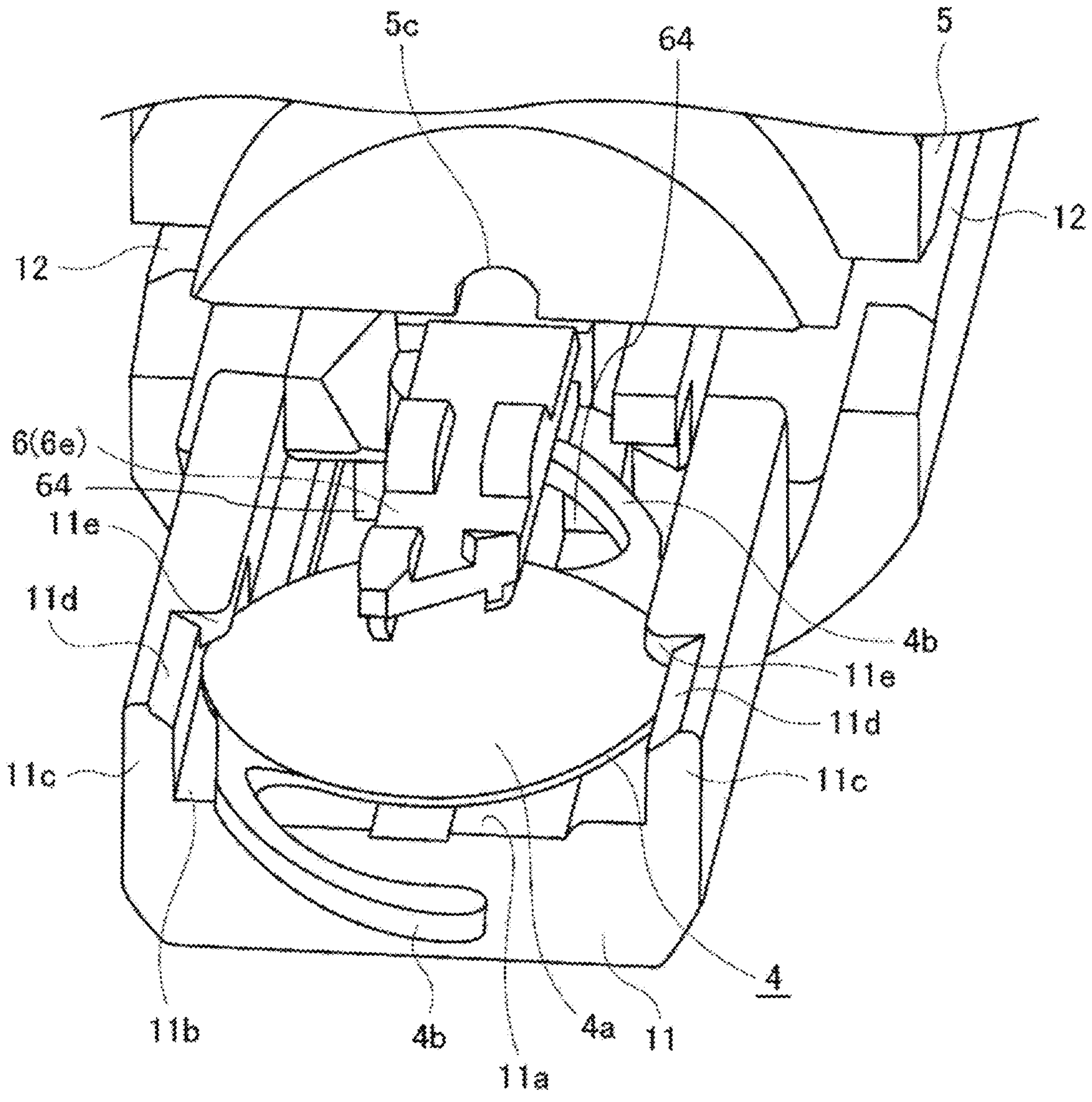
FIG. 7 is a perspective view showing the structure and the arrangement of the leading end portion of an injector main body according to Embodiment 1.

FIG. 7 is a perspective view showing the structure and the arrangement of the leading end portion of an injector main body according to Embodiment 1.

Figure 3:
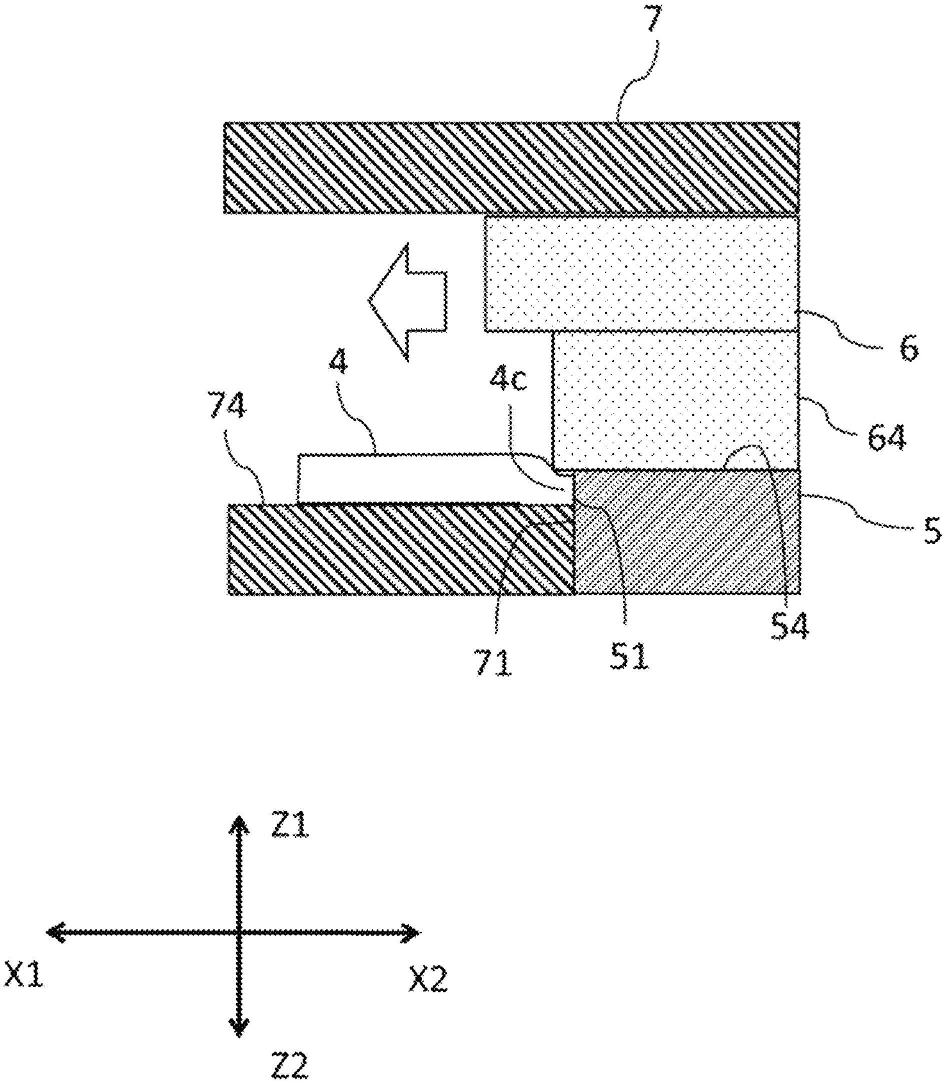
FIG. 3 is a diagram indicating a state in which, in the schematic partial cross-sectional view of the intraocular lens injector shown in FIG. 1, a downward step extending downward and forward is formed somewhere between an inner-circumference lower portion of the injector main body and an inner-circumference lower portion of an injection tube, and thus a rear side of the upper surface of the intraocular lens is caught between the downward step and the slider while the intraocular lens is being advanced.

Note that the configurations shown in FIGS. 6 and 7 of the present application are similar to those shown in FIGS. 3 and 6 of Patent Document 1. For this reason, among the reference signs shown in FIGS. 6 and 7 of the present application, reference signs that are not described in the present specification are as described in Patent Document 1.

The intraocular lens injector 1 is used to inject the intraocular lens 4 into an eye.

Intraocular Lens

In the embodiment of the present invention, as an example of the intraocular lens, there is provided a one-piece type intraocular lens 4 made of a soft material such as silicone elastomer or soft acrylic, and the intraocular lens 4 includes a circular optical portion 4*a* that performs an optical function, and two support portions 4*b* that extend outward in a curved manner from two positions on an outer circumferential portion of the optical portion 4*a*.

A case where the optical portion 4*a* of the intraocular lens 4 and the base ends of the respective support portions 4*b* connected to the optical portion 4*a* are made of a soft material is described by way of example. This configuration facilitates folding of the intraocular lens 4. Note that the distal ends of the respective support portions 4*b* may also be made of a soft material, or may be made of a hard material (e.g., polyethylene, PMMA, etc.).

In Embodiment 1, the intraocular lens 4 is advanced using the slider 6, but, to be exact, the slider 6 pushes the outer circumference of the optical portion 4*a* and thus the intraocular lens 4 is advanced. In the present specification, this is referred to merely as "pushing the intraocular lens 4" for convenience in the description.

Intraocular Lens Injector

The intraocular lens injector 1 includes the injector main body 5, the slider 6, the injection tube 7, a rotary member 8, the plunger 9, and the rod 10. These constituent elements are each preferably constituted by a resin molded product.

The injector main body 5 and the injection tube 7 have hollow structures and are connected to each other to thereby form a hollow body.

The slider 6 is attached to the injector main body 5.

The injection tube 7 is disposed so as to be in communication with a leading end portion of the injector main body 5. The injection tube 7 and the leading end portion of the injector main body 5 may be integrally molded, or may be separately molded and combined by attaching the injection tube 7 to the leading end portion. The injection tube 7 includes a hollow injection tube body 7*a* and a narrow tubular nozzle portion 7*b*. In this case, a lens setting portion 11 of the injector main body 5, together with the intraocular lens 4 set thereon, is housed and disposed in the injection tube body 7*a* of the injection tube 7. An injection hole 7*c* is formed in the upper surface of the injection tube body 7*a*. The injection hole 7*c* is a hole through which a viscoelastic substance (e.g., sodium hyaluronate etc.) is injected. The viscoelastic substance injected through the injection hole 7*c* is supplied to the intraocular lens 4 that is set on the lens setting portion 11.

The rotary member 8 is rotatably connected to the rear end portion of the injector main body 5.

The plunger 9 is disposed coaxially with the injector main body 5. A part of the plunger 9 is disposed inside the injector main body 5 via the rotary member 8. The other part of the plunger 9 may be disposed protruding rearward from the rotary member 8.

The rod 10 is disposed inside the hollow body formed by the injector main body 5 and the injection tube 7. The rod 10 is coupled to the plunger 9 and serves to advance the intraocular lens 4. Note that the rod 10 and the plunger 9 may be integrally molded.

As shown in FIG. 7, the lens setting portion 11 includes a bottom surface portion 11*a*, lens receiving portions 11*b*, and lens guide portions 11*c*. The lens receiving portions 11*b* receive and support the intraocular lens 4 from below. The intraocular lens injector 1 is of a preload type in which the intraocular lens 4 is set on the lens setting portion 11 of the injector main body 5 beforehand. Therefore, the intraocular lens 4 is one of the constituent elements of the intraocular lens injector 1. However, in carrying out the present invention, the intraocular lens injector 1 is not necessarily required to be of the preload type.

An example of the configuration of the intraocular lens injector 1 excluding a space 72 for accommodating a rear side 4*c* of the intraocular lens 4, which is one of the features of the present invention, can be expressed as follows.

"An intraocular lens injector 1, including:

an injector main body 5 constituted by a hollow body;

a lens setting portion 11 provided inside the injector main body 5;

a slider 6 for advancing an intraocular lens 4 set on the lens setting portion 11;

a rod 10 for further advancing the intraocular lens 4 that has been advanced using the slider 6; and an injection tube 7 that is separate from the injector main body 5 and is connected to the leading end portion of the injector main body 5, wherein the injection tube 7 includes a hollow injection tube body 7*a* and a tubular nozzle portion 7*b*."

Position and Shape of Space and Limit of Advance of Slider

In Embodiment 1, a case where a limit L of the advance of a slider lower portion 64 is located in the vicinity of connection portions 51 and 71 is described by way of example. In this example, the technical idea of the present invention is reflected in the shape of the connection portion 71 (corresponding to a position α) of the injection tube 7 where the injector main body 5 and the injection tube 7 are connected to each other. Note that, to be exact, the above-mentioned content should be expressed as "the connection portion where the injector main body 5 and the injection tube body 7*a* are connected to each other" in the embodiment of the present invention, but it is referred to simply as the "injection tube 7" for convenience in the description.

Figure 8:
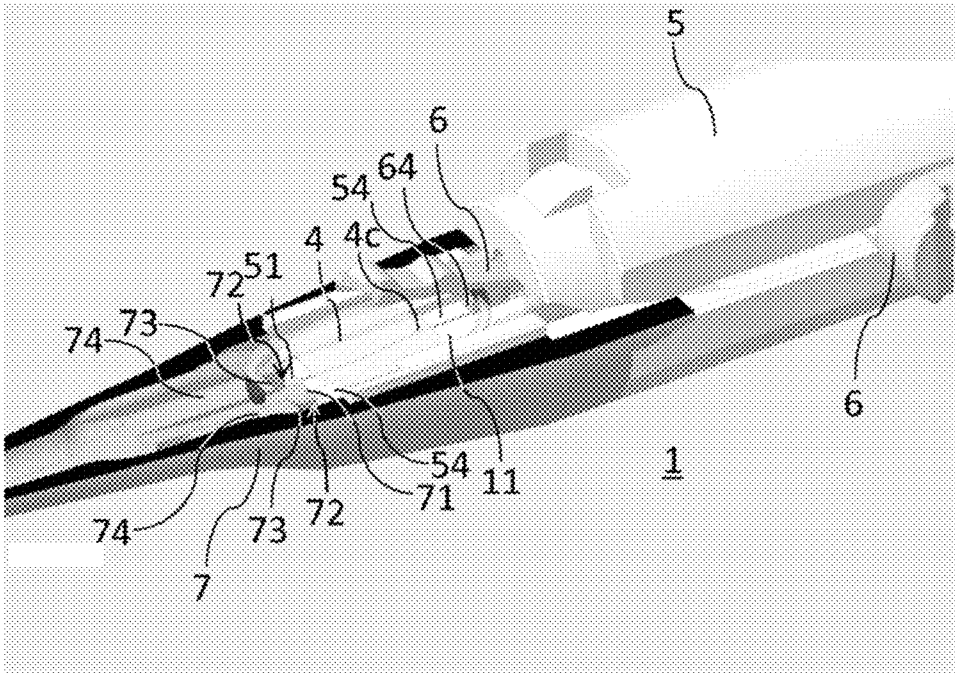
FIG. 8 is an exploded perspective view in which a connection portion where an injector main body and an injection tube of the intraocular lens injector (preload type) according to Embodiment 1 are connected to each other is exposed, and shows a state in which a slider has not been advanced yet.
Figure 8:
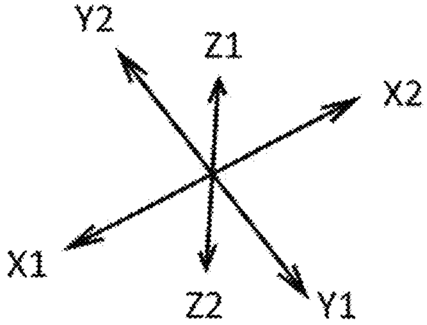

FIG. 8 is an exploded perspective view in which the connection portion where the injector main body and the injection tube of the intraocular lens injector (preload type) according to Embodiment 1 are connected to each other is exposed, and shows a state in which the slider has not been advanced yet.

Figure 9:
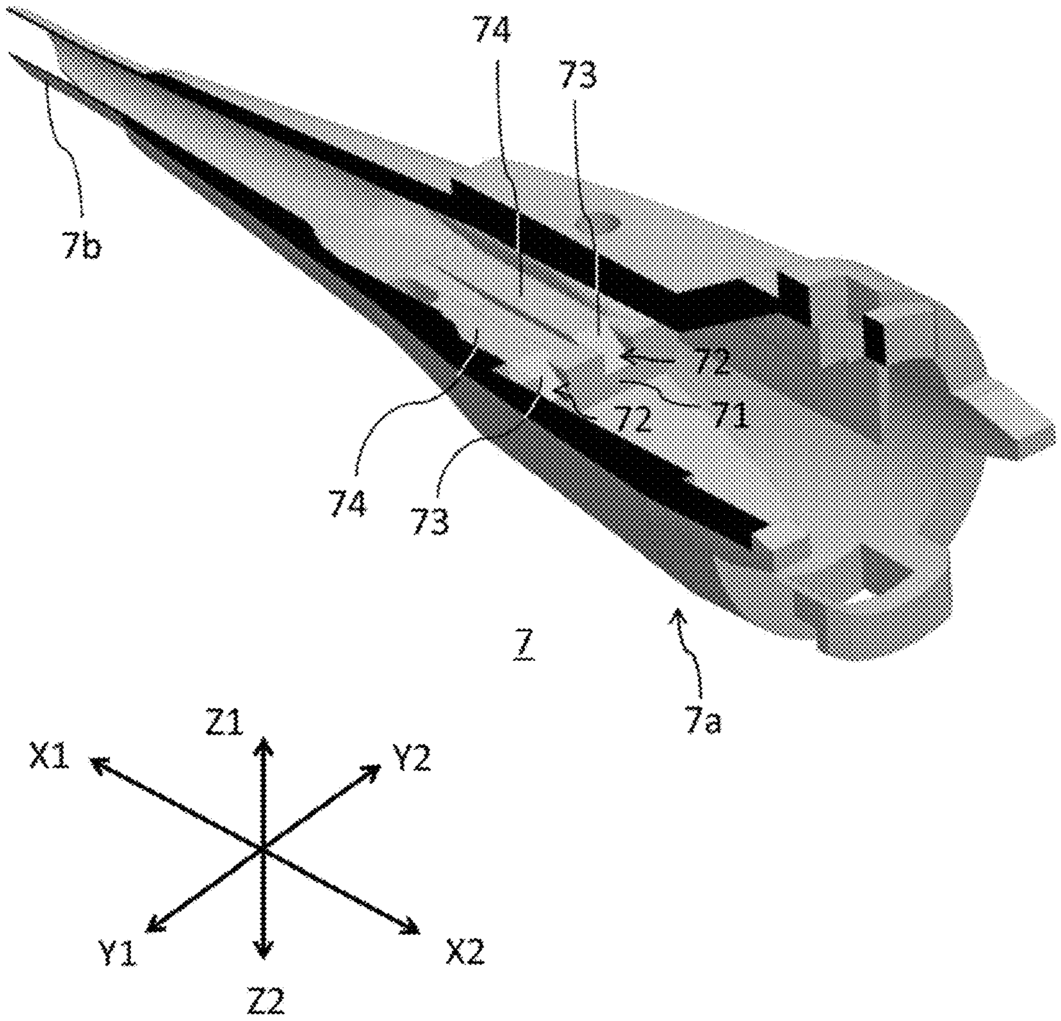
FIG. 9 is an exploded perspective view of the injection tube in FIG. 8.

FIG. 9 is an exploded perspective view of the injection tube in FIG. 8.

Figure 10:
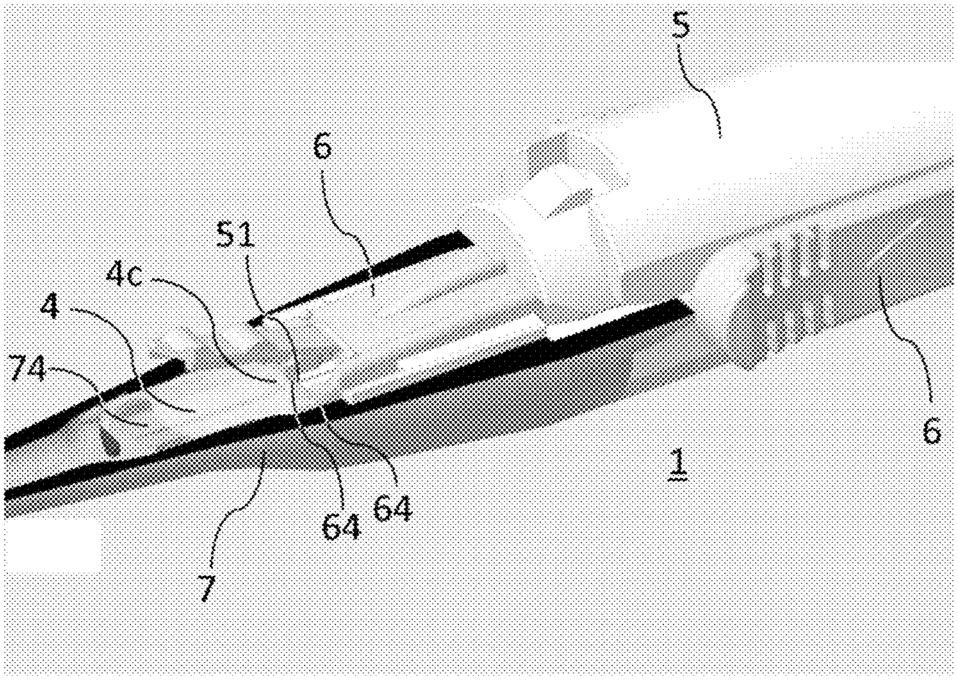
FIG. 10 is an exploded perspective view in which a connection portion where an injector main body and an injection tube of the intraocular lens injector (preload type) according to Embodiment 1 are connected to each other is exposed, and shows a state in which a slider has been advanced.
Figure 10:
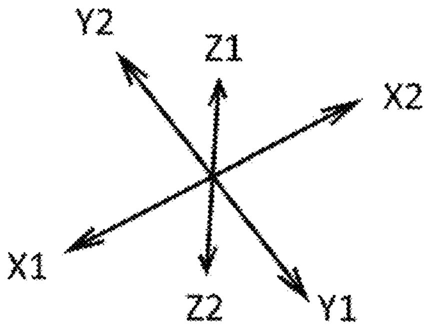

FIG. 10 is an exploded perspective view in which the connection portion where the injector main body and the injection tube of the intraocular lens injector (preload type) according to Embodiment 1 are connected to each other is exposed, and shows a state in which the slider has been advanced.

One of the features of the present invention is that the front limit L of the range of motion of the slider lower portion 64 is located within a region above the space 72. The rear side 4*c* of the intraocular lens 4 moves downward due to the space 72, and the intraocular lens 4 is released from being caught by the slider 6 when the advance of the slider 6 is finished, that is, when the advance of the rod 10 is started. FIG. 10 shows a state in which the slider 6 is advanced and reaches the limit L (the same applies to the right diagram in FIG. 4 and the right diagram in FIG. 5).

This configuration is employed with the following intent. If such an error that an inner-circumference lower portion 74 of the injection tube 7 is one level lower than an inner-circumference lower portion 54 of the injector main body 5 occurs as shown in the right diagram in FIG. 4 and the right diagram in FIG. 5, the intraocular lens 4 may be caught. On the other hand, if only the intraocular lens 4 is released from being caught when the advance of the slider 6 is finished, it will be possible to prevent the intraocular lens 4 from being damaged due to the advance of the rod 10. It is the above-mentioned configuration that defines the positional relationship between the limit L of the range of motion in the X-direction of the slider lower portion 64 and the position in the X-direction of the space 72 from this viewpoint.

As a result, even when the rod 10 is advanced, it is possible to prevent the rear side 4*c* of the intraocular lens 4 from being damaged (see a portion indicated by an arrow denoted by reference sign 72). In addition, the manufacturing accuracy of the injector main body 5 and the injection tube 7 need not be significantly improved. In other words, the errors in the manufacturing accuracy become acceptable due to the accommodation space 72 provided at the inner-circumference lower portion.

The front limit L of the range of motion of the slider lower portion 64 is preferably located at a position in the space 72, for example, within a range between the connection portion 71 connected to the injector main body 5, that is, the rear end of the space 72, and a position away therefrom by half (preferably ¼) the length in the front-rear direction of the space 72.

It is preferable that the space 72 into which a part of the rear side 4*c* of the intraocular lens 4 can move downward when the intraocular lens 4 is advanced using the slider 6 is provided at the inner-circumference lower portion 74 of the connection portion 71 of the injection tube 7 connected to the injector main body 5.

Figure 4:
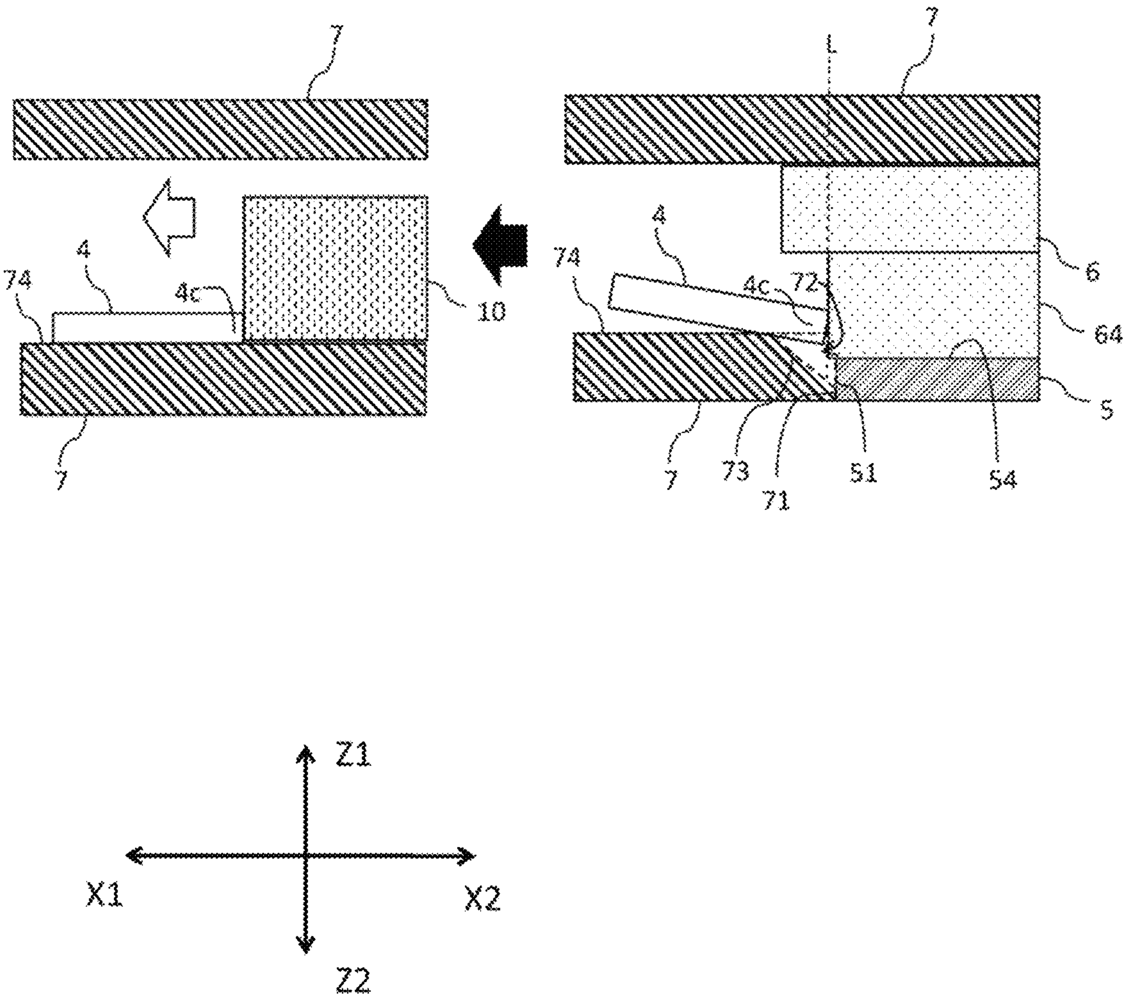
FIG. 4 shows a diagram (on the right side) indicating a state in which, in the schematic partial cross-sectional view of the intraocular lens injector shown in FIG. 1, even though an upward step is formed somewhere between the inner-circumference lower portion of the injector main body and the inner-circumference lower portion of the injection tube, it is possible to prevent the rear side of the upper surface of the intraocular lens from being caught between the upward step and the slider by forming a space for accommodating a part of the rear side of the intraocular lens at the corresponding position, and a diagram (on the left side) indicating a state in which the intraocular lens is properly pushed toward the nozzle portion using a rod.
Figure 5:
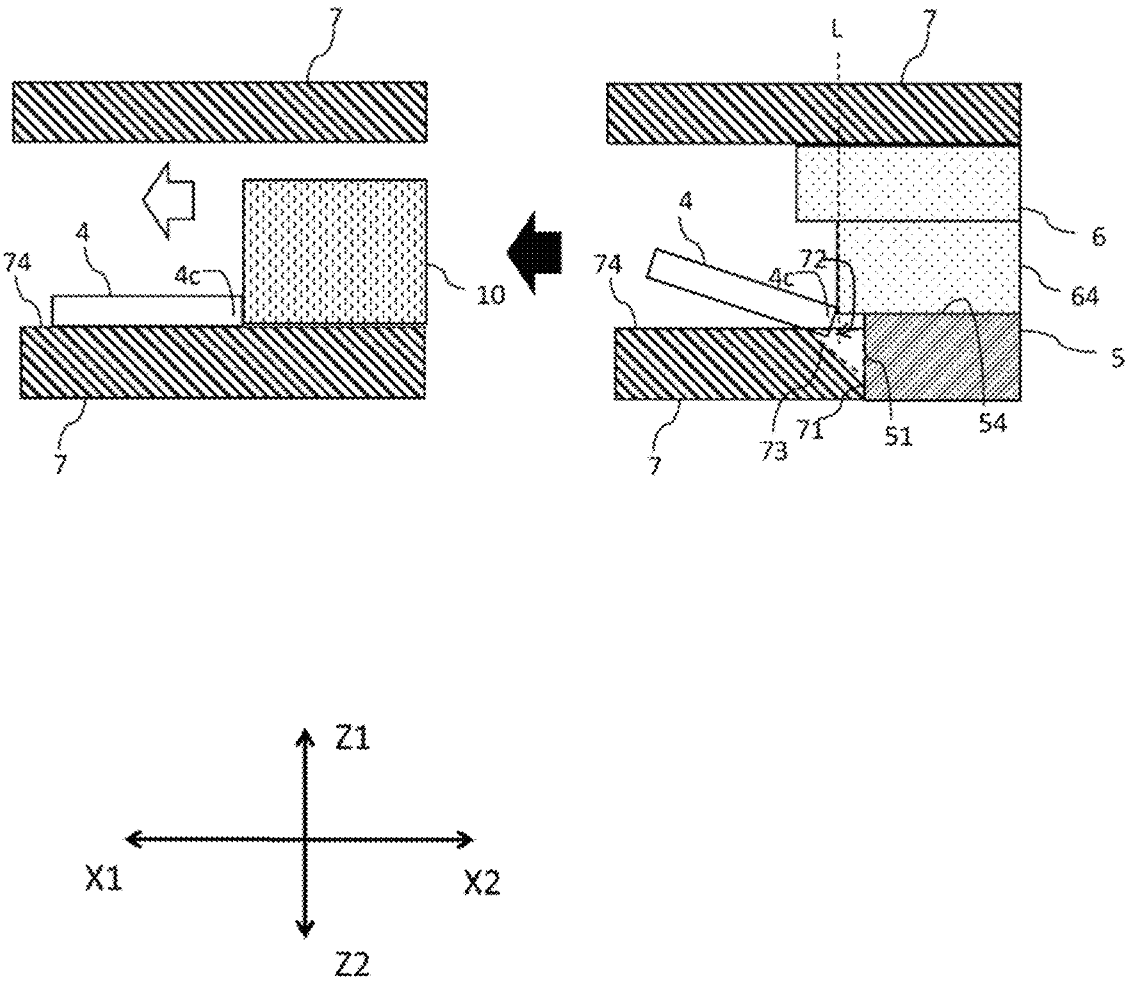
FIG. 5 shows a diagram (on the right side) indicating a state in which, in the schematic partial cross-sectional view of the intraocular lens injector shown in FIG. 1, even though a downward step is formed somewhere between the inner-circumference lower portion of the injector main body and the inner-circumference lower portion of the injection tube, it is possible to prevent the rear side of the upper surface of the intraocular lens from being caught between the downward step and the slider by forming a space for accommodating a part of the rear side of the intraocular lens at the corresponding position, and a diagram (on the left side) indicating a state in which the intraocular lens is properly pushed toward the nozzle portion using the rod.

There is no limitation on the shape of "the space 72 into which a part of the rear side 4*c* of the intraocular lens 4 can move" as long as the space 72 is provided at the inner-circumference lower portion 74 of the connection portion 71 of the injection tube 7 connected to the injector main body 5 when the advance of the intraocular lens 4 by the slider 6 is finished. Also, there is no limitation on the size of the space 72 as long as the space 72 can temporarily accommodate a part of the rear side 4*c* of the intraocular lens 4 as shown in FIGS. 4 and 5 when the advance of the intraocular lens 4 by the slider 6 is finished.

The space 72 may be, for example, a space formed by cutting the inner-circumference lower portion 74 of the connection portion 71 of the injection tube 7 connected to the injector main body 5. The space 72 may also be formed by bending the connection portion 71 of the injection tube 7 (the entire inner-circumference lower portion 74 of the injection tube 7) downward instead of cutting it. However, in this case, it is necessary to design the intraocular lens injector 1 so as to be capable of containing bulky components thereinside. Accordingly, it is preferable to form a cutout 73.

Figure 2:
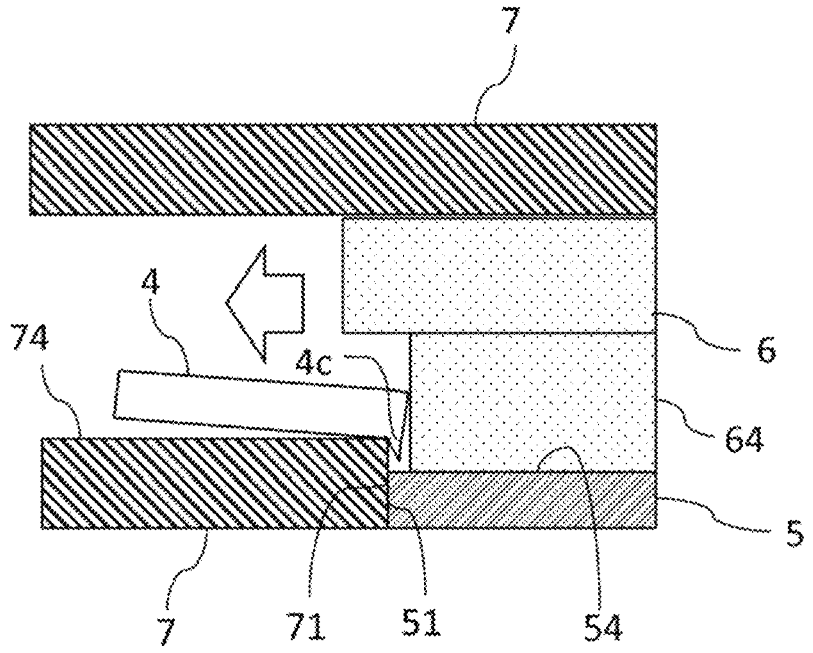
FIG. 2 is a diagram indicating a state in which, in the schematic partial cross-sectional view of the intraocular lens injector shown in FIG. 1, an upward step extending upward and forward is formed somewhere between an inner-circumference lower portion of the injector main body and an inner-circumference lower portion of an injection tube, and thus a rear side of the upper surface of the intraocular lens is caught between the upward step and the slider while the intraocular lens is being advanced.
Figure 2:
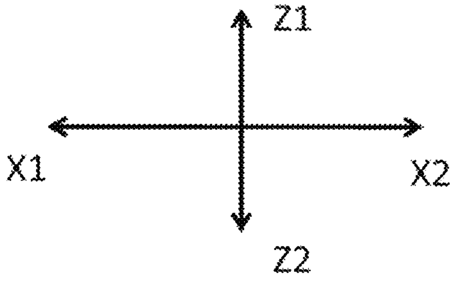

The shape of this cutout 73 is preferably a chamfered shape having an inclined surface. If a chamfered shape is employed, it is sufficient that such a slope angle of the chamfered surface that prevents the intraocular lens 4 from being caught by the slider 6 as shown in FIGS. 2 and 3 when the intraocular lens 4 is advanced using the slider 6 is determined while the height in the Z-direction of the connection portion 71 (specifically, the inner-circumference lower portion 74) of the injection tube 7 is reduced by the maximum thickness of the optical portion 4*a* of the intraocular lens 4. It is preferable that the slope of the chamfered surface is not too steep. The angle of the slope with respect to the XY plane is preferably 70° or less, and more preferably 50° or less. There is no limitation on the lower limit. However, if the slope angle is too small, the slope has to extend in the X-direction of the injection tube 7, and thus the lower limit is set to, for example, 30° or 40°.

The overall shape of the cutout 73 may be a chamfered shape as shown in FIGS. 8 to 10, or the cutout 73 may be formed such that only the front side of the cutout 73 has a chamfered shape and the rear side thereof, that is, the connection portion 71, is a step that is lower by a certain numerical value than the height of the injector main body 5. In other words, it is preferable that at least the front side of the cutout 73 has a chamfered shape.

The space 72 may have a depth in the direction Z2 corresponding to the sum of the manufacturing errors of the components, the positioning errors of the components, and the maximum thickness of the optical portion 4*a* of the intraocular lens 4. Specifically, the space may have a depth of 0.2 to 5.0 mm (preferably 0.5 to 2.0 mm).

If a chamfered shape is employed, the above-mentioned dimension may be determined in accordance with the slope angle of the chamfered surface.

It is preferable to employ the following configuration from the viewpoint that the rear side 4*c* of the intraocular lens 4 reliably moves into the space when the advance of the intraocular lens 4 by the slider 6 is finished. That is, in Embodiment 1, it is preferable that, as viewed from the front side, a position in the width direction (Y-direction) of a portion of the slider 6 that comes into contact with the inner-circumference lower portion 54 of the injector main body 5 is encompassed in a position in the width direction (Y-direction) of the space 72.

This configuration is employed with the following intent. The original reason why the intraocular lens 4 is caught by the slider 6 as shown in FIGS. 2 and 3 is that, when a portion of the slider 6 (e.g., slider lower portion 64) abuts against the outer circumference of the optical portion 4*a* of the intraocular lens 4 and pushes the intraocular lens 4, the slider lower portion 64 passes over the inner-circumference lower portion 74 of the injection tube 7 while catching the intraocular lens 4 thereunder (FIGS. 2 and 3).

Now, from another viewpoint of a reason why the intraocular lens 4 is damaged, it is sufficient that, as viewed from the front side, the space 72 is provided at at least the connection portion 71 (specifically, inner-circumference lower portion 74) of the injection tube 7 that corresponds to the width direction of a portion at which the slider lower portion 64 is located.

FIG. 9 shows a configuration in which this idea is reflected. That is, in FIG. 9, the cutout 73 having a chamfered shape (with a slope angle of 45°) is provided at the inner-circumference lower portion 74 of the connection portion 71 of the injection tube 7 that is disposed forward of the slider lower portion 64. In Embodiment 1, the limit L of the advance of the slider lower portion 64 is located above this cutout 73.

The width in the Y-direction of the space 72 may be larger by a certain margin than the width in the Y-direction of the slider lower portion 64. The width in the Y-direction of the space 72 may be set to be larger by a margin of 0.1 mm or more (or 0.2 mm or more; the upper limit is, for example, 1 mm) than the width in the Y-direction of the slider lower portion 64. In the case of not using a specific numerical value for this margin, the width in the Y-direction of the space 72 may be preferably, for example, 1.1 to 1.5 times as large as the width in the Y-direction of the slider lower portion 64. The space 72 may be provided over the entire inner-circumference lower portion 74 of the connection portion 71 of the injection tube 7.

However, when the space 72 is provided over the entire inner-circumference lower portion 74, the shape and the size of the space 72 are determined so as to prevent the slider lower portion 64 from failing to come into contact with the intraocular lens 4 due to the entire intraocular lens 4 dropping into the space 72. The expression "a part of the rear side 4*c* of the intraocular lens 4 can move downward" does not encompass a case where the slider lower portion 64 fails to come into contact with the intraocular lens 4 due to the entire rear side 4*c* of the intraocular lens 4 dropping into the space 72.

By setting the slope angle of the chamfered surface to be within the range above, and/or providing the space 72 at only the connection portion 71 (specifically, the inner-circumference lower portion 74) of the injection tube 7 that corresponds to the width direction of a portion at which the slider lower portion 64 is located, the greater part of the intraocular lens 4 is placed on the flat inner-circumference lower portion 74 located forward of the space 72, and even if the height is reduced by the maximum thickness of the intraocular lens 4, the rear side 4*c* of the intraocular lens 4 is merely displaced slightly downward. On the other hand, the reason why the intraocular lens 4 is caught as shown in FIGS. 2 and 3 is that there is no room for the rear side 4*c* of the intraocular lens 4 when the advance of the intraocular lens 4 by the slider 6 is finished. Accordingly, even if the rear side 4*c* of the intraocular lens 4 is merely displaced slightly downward as in the example, it is possible to sufficiently prevent the rear side 4*c* of the intraocular lens 4 from being caught.

As a result, it is possible to release the intraocular lens 4 from being caught between the slider 6 and the injection tube 7 when the advance of the intraocular lens 4 by the slider 6 is finished.

In the case where the space 72 is provided at only the connection portion 71 (specifically, inner-circumference lower portion 74) of the injection tube 7 that corresponds to the width direction of a portion at which the slider lower portion 64 is located (i.e., the space 72 is provided on only a portion of the width in the Y-direction of the inner-circumference lower portion 74 of the injection tube 7), even if a part of the rear side 4*c* of the intraocular lens 4 drops into the space 72, the other part of the intraocular lens 4 remains placed on a portion other than the space 72, that is, the flat inner-circumference lower portion 74 of the injection tube 7, thus making it possible to prevent the rear side 4*c* of the intraocular lens 4 from excessively dropping into the space 72.

An expression that collectively encompasses these cases is "a position in the width direction of a portion (e.g., slider lower portion 64) of the slider 6 that comes into contact with the inner-circumference lower portion 54 of the injector main body 5 is encompassed in a position in the width direction of the space 72".

Other Embodiments

The present invention is not limited to Embodiment 1 described above, and encompasses embodiments to which various modifications and refinements are added as long as specific effects obtained by the constituent requirements of the invention or combinations thereof can be derived.

Although a case where the injector main body 5 and the injection tube 7 are separate members has been described by way of example in Embodiment 1, the present invention is not limited thereto. For example, the injector main body 5 and the injection tube 7 may be integrally and inseparably formed. In this case, a portion that includes the nozzle portion 7*b* and has an external appearance that is tapered forward is taken as the injection tube 7. The injector main body 5 and the injection tube 7 are collectively referred to as a "hollow body".

Although a case where the cutout 73 is provided at the connection portion 71 (specifically, inner-circumference lower portion 74) of the connection portions 51 and 71 where the injector main body 5 and the injection tube 7 are connected to each other has been described by way of example in Embodiment 1, the present invention is not limited thereto. Furthermore, although a case where the limit L of the advance of the slider lower portion 64 is located in the vicinity of the connection portions 51 and 71 has been described by way of example, the present invention is not limited thereto. It is sufficient that the above-mentioned space 72 is provided at a position α located somewhere on the inner-circumference lower portion of the hollow body, that is, somewhere within a range between the inner-circumference lower portion 54 of the injector main body 5 and the inner-circumference lower portion 74 of the injection tube 7, the front limit of the range of motion of a portion of the slider that abuts against the outer circumference of the optical portion of the intraocular lens being encompassed above the position α.

One of the inspirations for achieving the present invention is a step that is accidentally formed at the inner-circumference lower portion. On the other hand, this is merely an inspiration, and this step is not a requirement for the intraocular lens injector 1 of the present invention. Furthermore, in addition to the step, there are various factors that cause the intraocular lens 4 to be caught by the slider 6. For example, as described in the section on the problems of the present invention, in the case where a clearance larger than necessary is present between the inner circumference of the injector main body 5 or injection tube 7 and the slider, even if no step is formed, the intraocular lens 4 may be caught between the inner circumference of the injector main body 5 or injection tube 7 and the slider.

Figure 11:
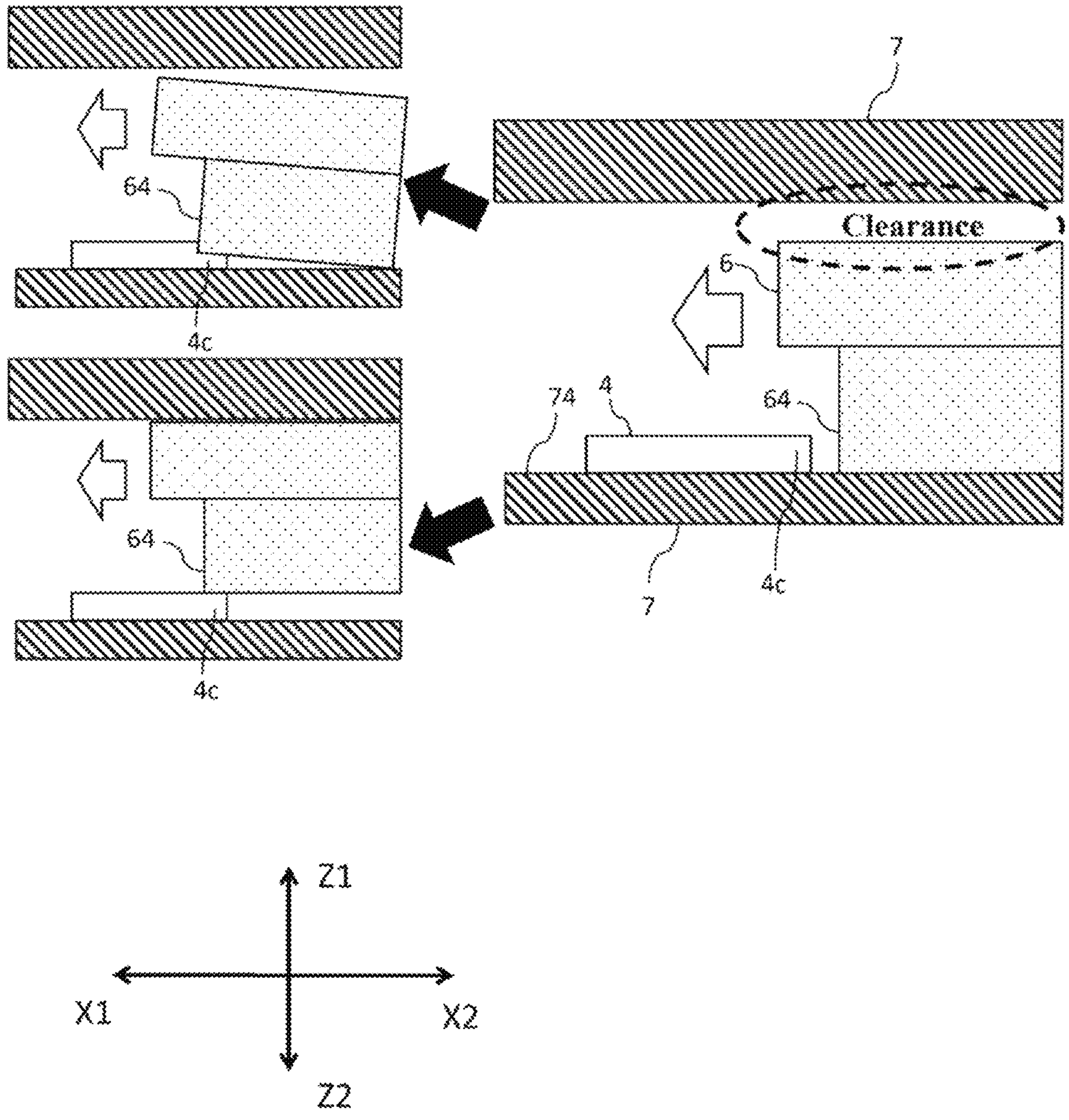
FIG. 11 is a diagram illustrating a state in which, in the case where a clearance larger than necessary is present between the inner circumference of an injector main body 5 or injection tube 7 and the slider, the intraocular lens is caught by the slider.

FIG. 11 is a diagram illustrating a state in which, in the case where a clearance larger than necessary is present between the inner circumference of the injector main body 5 or injection tube 7 and the slider, the intraocular lens is caught by the slider.

As shown in the upper left diagram in FIG. 11, when the above-mentioned clearance is present on the inner-circumference upper portion, the slider 6 is inclined upward inside the injector main body 5 or injection tube 7, and the slider lower portion 64 moves onto the intraocular lens 4, so that the intraocular lens may be caught by the slider.

As shown in the lower left diagram in FIG. 11, when the above-mentioned clearance is present on the inner-circumference lower portion, the slider 6 floats upward inside the injector main body 5 or injection tube 7, and the slider lower portion 64 moves onto the intraocular lens 4, so that the intraocular lens may be caught by the slider.

The present invention is characterized in that, even if the step is present due to manufacturing errors, or the above-mentioned factors (e.g., clearance) are present, the accommodation space 72 (cutout 73 (chamfered shape, depression) etc.) is provided beforehand at the inner-circumference lower portion such that the limit L of the advance of a portion (e.g., slider lower portion 64) of the slider 6 that abuts against the outer circumference of the optical portion 41 of the intraocular lens 4 is encompassed above the space 72. Providing this space 72 makes it possible to prevent the intraocular lens 4 from being caught without significantly improving the manufacturing accuracy (specifically, the manufacturing accuracy of the injector main body and the injection tube), and thus suppress damage to the intraocular lens 4.

Even if the inner-circumference lower portion (i.e., the region between the inner-circumference lower portion 54 of the injector main body 5 and the inner-circumference lower portion 74 of the injection tube 7) is flush due to there being no manufacturing errors, and the clearance larger than necessary is not provided, advantageous effects are exhibited by providing beforehand the space 72 for accommodating the rear side 4*c* of the intraocular lens 4 below the limit L of the advance of a portion of the slider 6 that abuts against the outer circumference of the optical portion 41 of the intraocular lens 4.

That is, in the case where the space 72 is provided, even if the manufacturing errors occur or the clearance is formed in the intraocular lens injector 1, the manufacturing errors or the clearance becomes acceptable due to the space 72, and thus use of an intraocular lens injector 1 that would have been discarded hitherto is allowed. This is a great practical advantage.

In another embodiment (referred to as "Embodiment 2" hereinafter), a case where the intraocular lens 4 is folded and released from the nozzle portion 7*b* using the plunger 9 (in turn, the rod 10) without providing the slider 6 is described by way of example. That is, a case where the advancing member is the plunger 9 (it is the rod 10 that comes into direct contact with the intraocular lens 4) is described by way of example. For content that is not described below, the descriptions of Embodiment 1 are incorporated by reference.

In Embodiment 2, the rod 10 is advanced to the vicinity of the discharge hole of the nozzle portion 7*b*. For this reason, the rod 10 (in turn, the lower portion of the rod 10) is positioned at only the center in the width direction of the connection portion 71 of the injection tube 7 connected to the injector main body 5. Accordingly, it is sufficient that the space 72 for accommodating the rear side 4*c* of the intraocular lens 4 is provided at at least the center in the width direction (Y-direction) of the connection portion 71 of the injection tube 7. This configuration is the converse of the configuration shown in FIG. 9 in which the space 72 is not provided at a portion located at the center in the width direction (Y-direction) of the connection portion 71 of the injection tube 7 through which the rod 10 passes, but the cutouts 73 having a chamfered shape that correspond to the slider lower portion 64 are provided on both sides in the Y-direction of the above-mentioned portion.

In Embodiment 2, unlike Embodiment 1 in which the limit L of the range of motion in the X-direction of the slider lower portion 64 is defined, the rod 10 has to be advanced to the vicinity of the discharge hole of the nozzle portion 7*b*. With this configuration, it seems that the rear side 4*c* of the intraocular lens 4 becomes tangled between the rod 10 and the injection tube 7 as shown in FIG. 3.

On the other hand, shaping at least the front side of the space 72 into a chamfered shape, that is, an inclined surface (preferably the cutout 73) facilitates the lower portion of the rod 10 to continue to push the intraocular lens 4 along the inclined surface, so that the lower portion of the rod 10 is unlikely to be placed on the intraocular lens 4.

If a chamfered shape is employed, it is sufficient that such a slope angle of the chamfered surface that prevents the intraocular lens 4 from being cut as shown in FIG. 2 or becoming tangled as shown in FIG. 3 when the intraocular lens 4 is advanced using the slider 6 is determined while the height of the connection portion 71 of the injection tube 7 is reduced by the maximum thickness of the optical portion 4*a* of the intraocular lens 4.

As a result, the lower portion of the rod 10 is prevented from being advanced while scraping off the upper side of the intraocular lens 4, and instead, the rod 10 can be advanced together with the intraocular lens 4 (i.e., in the normal state). Shaping the space 72 into a chamfered shape has such an advantage.

Note that, in Example 2, the expression "a part of the rear side 4*c* of the intraocular lens 4 can move downward" does not encompass a case where the lower portion of the rod 10 fails to come into contact with the intraocular lens 4 due to the entire rear side 4*c* of the intraocular lens 4 dropping into the space 72.

One of the inspirations for achieving the aspect according to Embodiment 2 is a difference in height between the inner-circumference lower portion 54 of the injector main body 5 and the inner-circumference lower portion 74 of the injection tube 7. On the other hand, this is merely an inspiration, and this difference in height is not a requirement for the intraocular lens injector 1 of the aspect according to Embodiment 2.

The aspect according to Embodiment 2 is characterized in that, even if the difference in height is present due to the manufacturing errors, the manufacturing errors become acceptable due to the accommodation space 72 being provided. In the case where the space 72 is provided beforehand, even if the inner-circumference lower portion 54 of the injector main body 5 and the inner-circumference lower portion 74 of the injection tube 7 are flush with each other due to there being no manufacturing errors, the manufacturing errors become acceptable due to the space 72 even in the intraocular lens injector 1 in which the manufacturing errors occur, and thus use of an intraocular lens injector 1 that would have been discarded hitherto is allowed. This is a great practical advantage.

With the aspect according to Embodiment 2, it is possible to provide the intraocular lens injector 1 capable of suppressing damage to the intraocular lens 4 without significantly improving the manufacturing accuracy of the injector main body 5 and the injection tube 7.

The configuration of Embodiment 2 can be summarized as follows.

The intraocular lens injector 1 may also be an intraocular lens injector 1 for injecting an intraocular lens 4 into an eye, including:

an injector main body 5 constituted by a hollow body;

a lens setting portion 11 provided inside the injector main body 5;

an advancing member for advancing the intraocular lens 4 set on the lens setting portion 11; and an injection tube 7 that is separate from the injector main body 5 and is connected to the front end portion of the injector main body 5, wherein, when a side in the optical axis direction (Z-direction) of the intraocular lens 4 that comes into contact with the lens setting portion 11 when the intraocular lens 4 is set on the lens setting portion 11 is defined as a bottom side (direction Z2), a side opposite to the bottom side is defined as a top side (direction Z1), a side toward which the intraocular lens 4 is advanced is defined as a front side (direction X1), a side opposite to the front side is defined as a rear side (direction X2), and a direction orthogonal to the Z-direction and X-direction is defined as a width direction (Y-direction), a space 72 into which a part of the rear side of the intraocular lens 4 can move downward when the intraocular lens 4 is advanced using the advancing member is provided at an inner-circumference lower portion 74 of a connection portion 71 of the injection tube 7 connected to the injector main body 5.

The space 72 may be formed by cutting the inner-circumference lower portion 74 of the connection portion 71 of the injection tube 7 connected to the injector main body 5, and as viewed from the front side, a position in the width direction of a portion of the advancing member that abuts against the outer circumference of the optical portion 4*a* of the intraocular lens 4 may be encompassed in a position in the width direction of the space 72.

The advancing member may be a rod 10 for advancing the intraocular lens 4 set on the lens setting portion 11.

REFERENCE SIGNS LIST

1 Intraocular lens injector
4 Intraocular lens
4*a* Optical portion
4*b* Support portion
4*c* Rear side (of intraocular lens)
5 Injector main body
51 Connection portion (of injector main body connected to injection tube body)
54 Inner-circumference lower portion (of injector main body)
6 Slider
64 Slider lower portion
7 Injection tube
71 Connection portion (of injection tube body connected to injector main body)
72 Space
73 Cutout (chamfered surface)
74 Inner-circumference lower portion (of injection tube)
7*a* Injection tube body
7*b* Nozzle portion
7*c* Injection hole
8 Rotary member
9 Plunger
10 Rod
11 Lens setting portion
11*a* Bottom surface portion
11*b* Lens receiving portion
11*c* Lens guide portion
L Limit of advance of slider lower portion

The invention claimed is:

1. An intraocular lens injector for injecting an intraocular lens into an eye, comprising:

a hollow body;

a lens setting portion provided inside the hollow body;

a slider for advancing the intraocular lens set on the lens setting portion; and a rod for further advancing the intraocular lens that has been advanced using the slider, wherein when a side in the optical axis direction (Z-direction) of the intraocular lens that comes into contact with the lens setting portion when the intraocular lens is set on the lens setting portion is defined as a bottom side (direction Z2), a side opposite to the bottom side is defined as a top side (direction Z1), a side toward which the intraocular lens is advanced is defined as a front side (direction X1), a side opposite to the front side is defined as a rear side (direction X2), and a direction orthogonal to the Z-direction and X-direction is defined as a width direction (Y-direction), the hollow body defines an inner-circumference bottom surface and an inner-circumference top surface, a space that extends downwardly from the inner-circumference bottom surface and into which a part of the rear side of the intraocular lens is capable of moving downward is provided at a position $\alpha$ on the inner-circumference bottom surface, and a front limit of a range of motion of a portion of the slider that abuts against an outer circumference of an optical portion of the intraocular lens is located above the position $\alpha$.

2. The intraocular lens injector according to claim 1, wherein the hollow body includes:

an injector main body; and an injection tube that is connected to a front end portion of the injector main body, and the position $\alpha$ is located somewhere within a range between the injector main body and the injection tube.

3. The intraocular lens injector according to claim 2, wherein the space is provided at a connection portion of the injection tube connected to the injector main body.

4. The intraocular lens injector according to claim 3, wherein the space is formed by cutting the position $\alpha$, and as viewed from a front side of the space, a position in a width direction of the portion of the slider that abuts against the outer circumference of the optical portion of the intraocular lens is encompassed in a position in a width direction of the space.

5. The intraocular lens injector according to claim 3, wherein the space has a chamfered shape.

6. The intraocular lens injector according to claim 2, wherein the space is formed by cutting the position $\alpha$, and as viewed from a front side of the space, a position in a width direction of the portion of the slider that abuts against the outer circumference of the optical portion of the intraocular lens is encompassed in a position in a width direction of the space.

7. The intraocular lens injector according to claim 2, wherein the space has a chamfered shape.

8. The intraocular lens injector according to claim 1, wherein the space is formed by cutting the position $\alpha$, and as viewed from a front side of the space, a position in a width direction of the portion of the slider that abuts against the outer circumference of the optical portion of the intraocular lens is encompassed in a position in a width direction of the space.

9. The intraocular lens injector according to claim 8, wherein the space has a chamfered shape.

10. The intraocular lens injector according to claim 1, wherein the space has a chamfered shape.

11. The intraocular lens injector according to claim 1, wherein the intraocular lens is set on the lens setting portion beforehand.

12. An intraocular lens injector for injecting an intraocular lens into an eye, the intraocular lens injector comprising:

a main body defining a main body inner circumference that has a top surface and a bottom surface with a connection portion;

an injection tube defining an injection tube inner circumference that decreases in size and that has a top surface, a bottom surface with a connection portion that abuts the main body bottom surface connection portion, and a cutout surface that slopes downwardly from the injection tube bottom surface and toward the main body bottom surface connection portion and that forms a space that is configured to receive a downwardly moving part of a rear side of the intraocular lens; and a rod configured to advance the intraocular lens out of the injection tube;

wherein the main body and injection tube define a lens advancing direction;

the cutout surface defines an end that abuts the main body bottom surface connection portion;

the cutout surface end is located below portions of the main body bottom surface connection portion that are aligned with the cutout surface end in the lens advancing direction.

13. The intraocular lens injector according to claim 12, wherein the cutout surface extends to the main body bottom surface connection portion.

14. The intraocular lens injector according to claim 12, wherein the intraocular lens injector comprises a preloaded intraocular lens injector;

the main body has a lens setting portion; and the intraocular lens is located in the lens setting portion.

15. An intraocular lens injector for injecting an intraocular lens into an eye, the intraocular lens injector comprising:

a main body defining a main body inner circumference that has a top surface, a bottom surface with a connection portion, and a lens setting portion;

a slider, including a lens engaging portion that engages an outer circumference of the interocular lens and has a front limit of range of motion, configured to push the intraocular lens out of the lens setting portion;

an injection tube defining an injection tube inner circumference that decreases in size and that has a top surface, a bottom surface with a connection portion that abuts the main body bottom surface connection portion, and a cutout surface that slopes downwardly from the injection tube bottom surface and toward the main body bottom surface connection portion and that forms a space that is configured to receive a downwardly moving part of a rear side of the intraocular lens; and a rod configured to advance the intraocular lens out of the injection tube;

wherein the space is aligned with the front limit of range of motion of the lens engaging portion.

16. The intraocular lens injector according to claim 15, wherein the intraocular lens injector comprises a preloaded intraocular lens injector; and the intraocular lens is located in the lens setting portion.

17. An intraocular lens injector for injecting an intraocular lens into an eye, the intraocular lens injector comprising:

a main body defining a main body inner circumference that has a top surface and a bottom surface with a connection portion;

an injection tube defining an injection tube inner circumference that decreases in size and that has a top surface, a bottom surface with a connection portion that abuts the main body bottom surface connection portion, and a cutout surface that slopes downwardly from the injection tube bottom surface and toward the main body bottom surface connection portion and that forms a space that is configured to receive a downwardly moving part of a rear side of the intraocular lens and that defines a depth that decreases with distance from the main body; and a rod configured to advance the intraocular lens out of the injection tube.

18. The intraocular lens injector according to claim 17, wherein the main body includes a lens setting portion;

the intraocular lens injector further comprises a slider, including a lens engaging portion that engages an outer circumference of the interocular lens, configured to push the intraocular lens out of the lens setting portion;

the lens engaging portion has a front limit of range of motion; and the space is aligned with the front limit of range of motion of the lens engaging portion.

19. The intraocular lens injector according to claim 18, wherein the intraocular lens injector comprises a preloaded intraocular lens injector; and the intraocular lens is located in the lens setting portion.

* * * * *